United States Patent [19]
Augustine

[11] Patent Number: 5,964,723
[45] Date of Patent: Oct. 12, 1999

[54] NORMOTHERMIC TISSUE HEATING WOUND COVERING

[75] Inventor: Scott D. Augustine, Bloomington, Minn.

[73] Assignee: Augustine Medical, Inc., Eden Prairie, Minn.

[21] Appl. No.: 08/786,713

[22] Filed: Jan. 21, 1997

Related U.S. Application Data

[63] Continuation-in-part of application No. 08/356,325, filed as application No. PCT/US93/05876, Jun. 18, 1993, abandoned, which is a continuation-in-part of application No. 07/900,656, Jun. 19, 1992, abandoned.

[51] Int. Cl.$^6$ .............................. A61F 7/00; A61F 13/00
[52] U.S. Cl. ................. 602/42; 602/2; 602/54; 607/96; 607/108
[58] Field of Search .................. 602/2, 41, 42, 602/46, 48, 56, 57; 128/888, 889, 887; 607/96, 99, 108, 109, 111, 112, 152; 604/113, 114

[56] References Cited

U.S. PATENT DOCUMENTS

| | | |
|---|---|---|
| 222,690 | 12/1879 | Goldschmidt . |
| 697,637 | 4/1902 | Lee . |
| 720,812 | 2/1903 | Johnson . |
| 1,384,467 | 7/1921 | Homan . |

(List continued on next page.)

FOREIGN PATENT DOCUMENTS

| | | |
|---|---|---|
| 0 424 165 | 4/1991 | European Pat. Off. . |
| 0 485 657 | 5/1992 | European Pat. Off. . |
| 0 638 300 A1 | 8/1993 | European Pat. Off. . |
| 0 607 472 | 7/1994 | European Pat. Off. . |
| 1 303 238 | 7/1962 | France . |
| 1 489 127 | 7/1967 | France . |
| 1 527 887 | 4/1968 | France . |
| 2 544 202 | 10/1984 | France . |
| 31 02 674 | 9/1982 | Germany . |
| 31 18 232 | 11/1982 | Germany . |
| 35 39 533 | 5/1987 | Germany . |
| 269 938 | 7/1950 | Switzerland . |
| 378 465 | 4/1964 | Switzerland . |
| 3090 | 6/1902 | United Kingdom . |
| 288 220 | 7/1927 | United Kingdom . |
| 2 082 919 | 3/1982 | United Kingdom . |
| 2 199 501 | 7/1988 | United Kingdom . |
| 2 261 822 | 6/1993 | United Kingdom . |
| 2 263 872 | 8/1993 | United Kingdom . |
| WO 89 04158 | 5/1989 | WIPO . |
| WO 93/19706 | 10/1993 | WIPO . |
| WO 94 00090 | 1/1994 | WIPO . |
| WO 96/10379 | 5/1996 | WIPO . |
| WO 96 15745 | 5/1996 | WIPO . |

OTHER PUBLICATIONS

International Search Report for PCT/US97/20585.

*Primary Examiner*—Richard J. Apley
*Assistant Examiner*—Kim M. Lee
*Attorney, Agent, or Firm*—Gray Cary Ware Freidenrich

[57] ABSTRACT

A non-contact heated wound covering preferably having a peripheral sealing ring covered by a layer to which is attached a heater and this assembly is attached to the skin with an adhesive so that the heater is held proximate the wound area in a non-contact position. The layer and peripheral sealing ring together define a treatment volume proximate the wound. The wound covering includes a programmable active heater control and the sealing ring may dispense water to control the humidity of the treatment volume. One form of active heat is an electrical resistive filament in variable geometric shapes providing versatility in application of heat to different types of wounds and wound area geometries. Another form of active heat is the transfer of a heated gas to the wound covering.

87 Claims, 19 Drawing Sheets

U.S. PATENT DOCUMENTS

| | | |
|---|---|---|
| 1,399,095 | 12/1921 | Webb, Sr. . |
| 1,777,982 | 10/1930 | Popp . |
| 1,920,808 | 8/1933 | Sander . |
| 1,979,082 | 10/1934 | Schwedenberg et al. . |
| 2,221,758 | 11/1940 | Elmquist . |
| 2,443,481 | 6/1948 | Sene . |
| 2,573,791 | 11/1951 | Howells . |
| 2,577,945 | 12/1951 | Atheton . |
| 2,599,523 | 6/1952 | Dorr . |
| 2,601,189 | 6/1952 | Wales, Jr. . |
| 2,632,443 | 3/1953 | Lesher . |
| 2,706,988 | 4/1955 | Weber . |
| 2,769,892 | 11/1956 | Collins . |
| 3,026,874 | 3/1962 | Stevens . |
| 3,528,416 | 9/1970 | Chamberlain . |
| 3,596,657 | 8/1971 | Eidus . |
| 3,610,238 | 10/1971 | Rich, Jr. . |
| 3,610,251 | 10/1971 | Sanderson . |
| 3,687,143 | 8/1972 | Schneeberger et al. . |
| 3,691,646 | 9/1972 | Ruffolo . |
| 3,782,377 | 1/1974 | Rychlik . |
| 3,814,095 | 6/1974 | Lubens . |
| 3,867,939 | 2/1975 | Moore . |
| 3,881,477 | 5/1975 | Von Otto . |
| 4,080,971 | 3/1978 | Leeper . |
| 4,134,399 | 1/1979 | Halderson . |
| 4,172,495 | 10/1979 | Zebuhr et al. . |
| 4,279,255 | 7/1981 | Hoffman . |
| 4,341,209 | 7/1982 | Schaar . |
| 4,382,441 | 5/1983 | Svedman ............................ 604/291 |
| 4,399,816 | 8/1983 | Spangler . |
| 4,484,574 | 11/1984 | DeRusha et al. . |
| 4,517,972 | 5/1985 | Finch, Jr. . |
| 4,540,412 | 9/1985 | Van Overloop ........................ 604/291 |
| 4,572,188 | 2/1986 | Augustine et al. . |
| 4,628,930 | 12/1986 | Williams . |
| 4,633,863 | 1/1987 | Filips et al. . |
| 4,641,641 | 2/1987 | Strock . |
| 4,641,643 | 2/1987 | Greer . |
| 4,667,666 | 5/1987 | Fryslie . |
| 4,890,608 | 1/1990 | Steer . |
| 4,925,743 | 5/1990 | Ikeda et al. ............................ 428/702 |
| 4,962,761 | 10/1990 | Golden . |
| 4,969,881 | 11/1990 | Viesturs ................................ 604/305 |
| 5,003,971 | 4/1991 | Buckley . |
| 5,025,777 | 6/1991 | Hardwick . |
| 5,053,024 | 10/1991 | Dvoretzky .............................. 604/291 |
| 5,060,662 | 10/1991 | Farnsworth, III ...................... 128/888 |
| 5,086,763 | 2/1992 | Hathman ................................ 602/42 |
| 5,107,832 | 4/1992 | Guibert et al. . |
| 5,135,518 | 8/1992 | Vera ...................................... 604/291 |
| 5,144,113 | 9/1992 | Hall et al. . |
| 5,144,958 | 9/1992 | Krueger et al. . |
| 5,170,781 | 12/1992 | Loomis . |
| 5,190,031 | 3/1993 | Guibert et al. . |
| 5,230,350 | 7/1993 | Fentress . |
| 5,431,622 | 7/1995 | Pyrozyk et al. ......................... 602/2 |
| 5,531,670 | 7/1996 | Westby et al. ........................ 602/41 |
| 5,609,619 | 3/1997 | Pompei ................................. 607/104 |
| 5,649,972 | 7/1997 | Hochstein ............................. 607/100 |
| 5,817,145 | 10/1998 | Augustine et al. ..................... 607/96 |

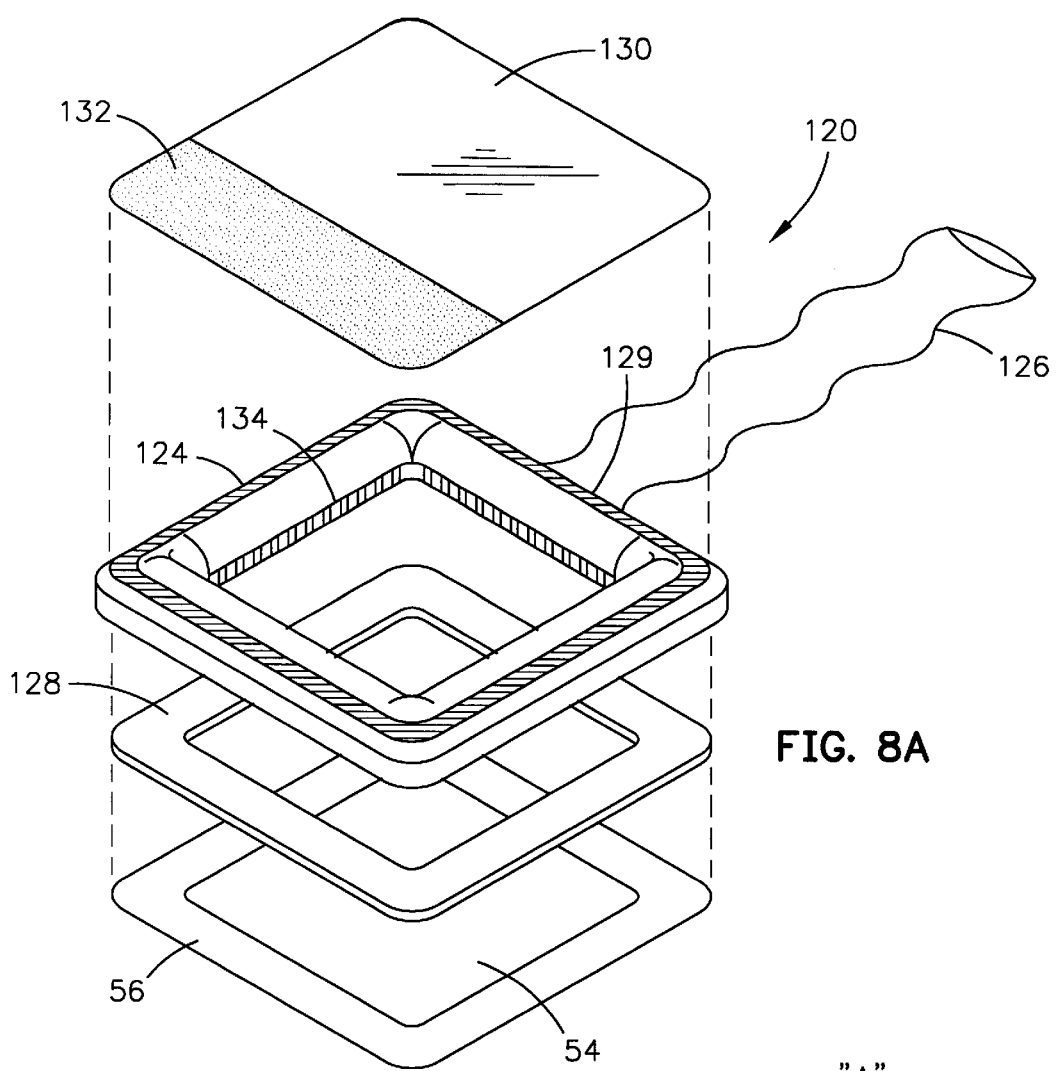
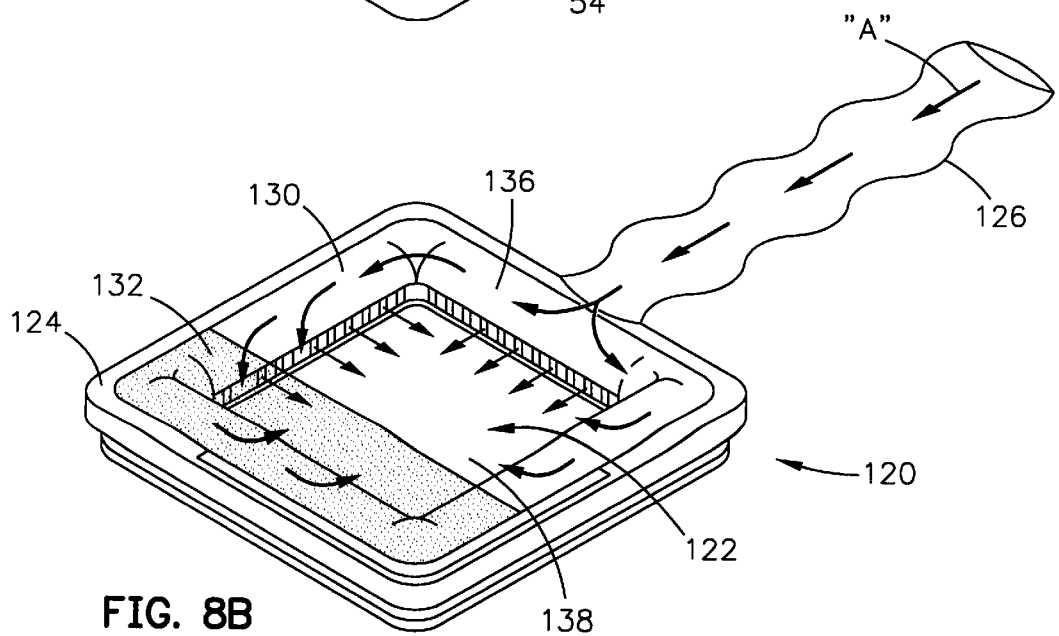

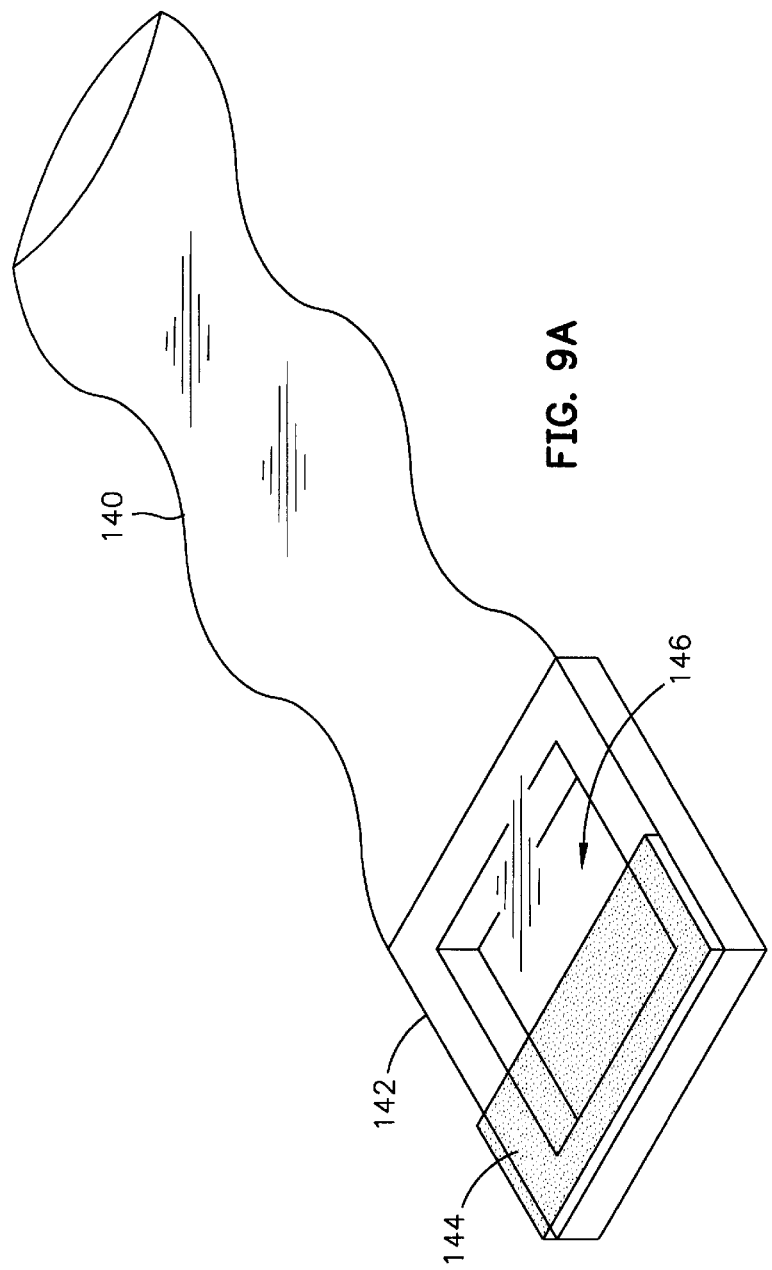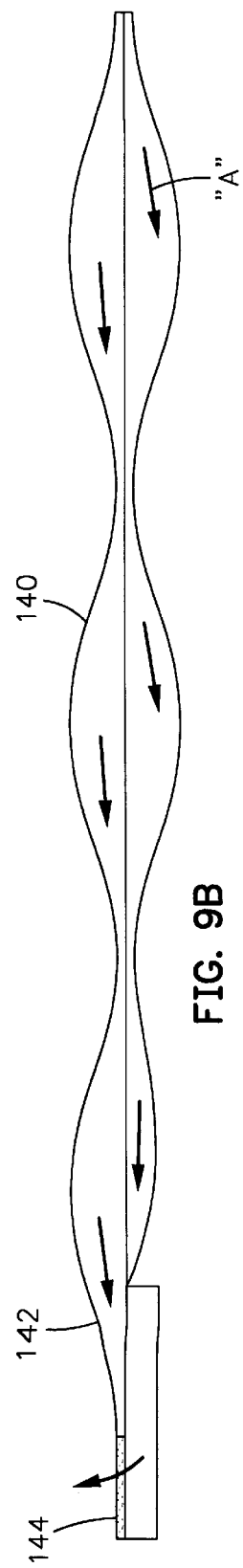

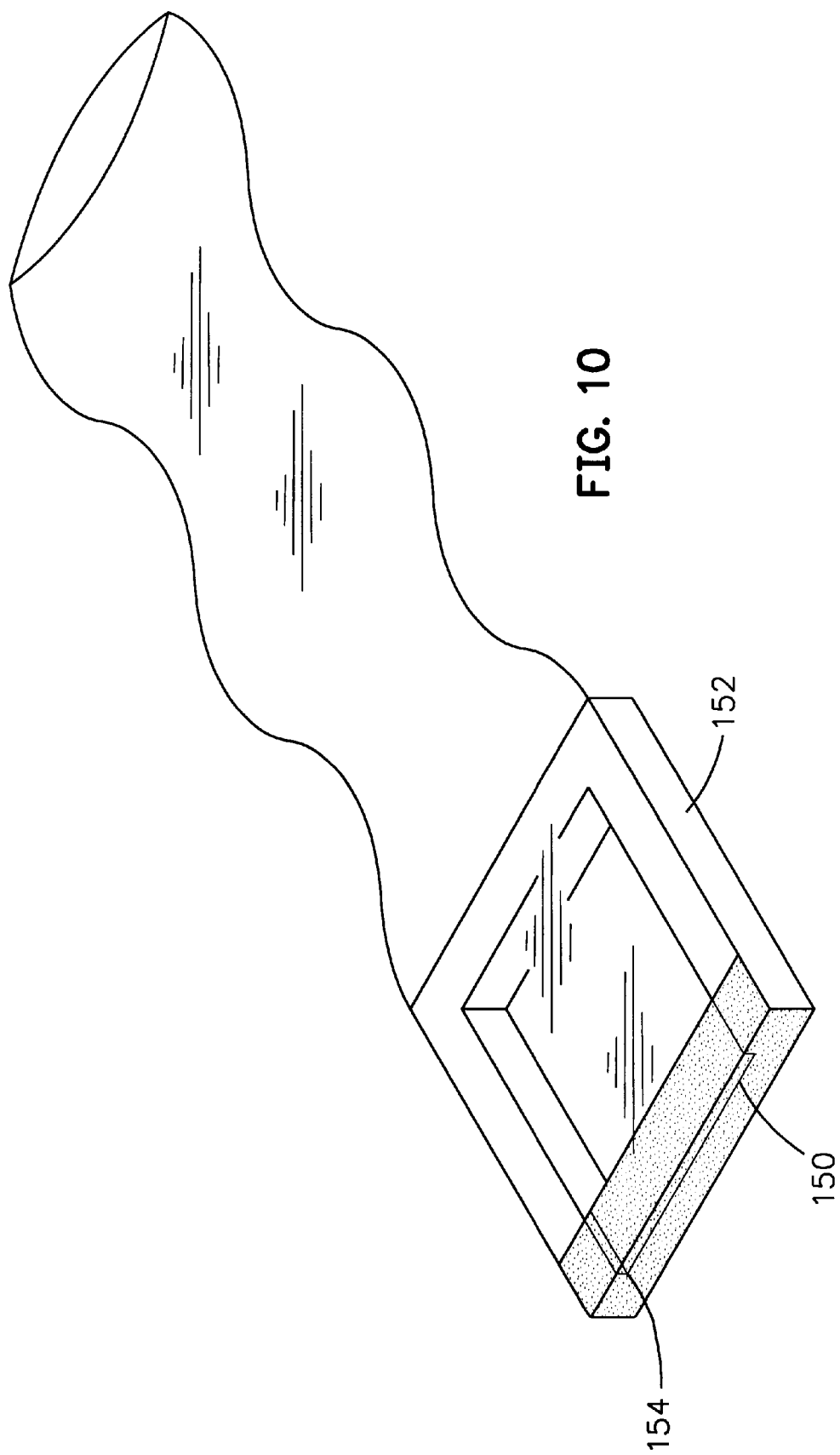

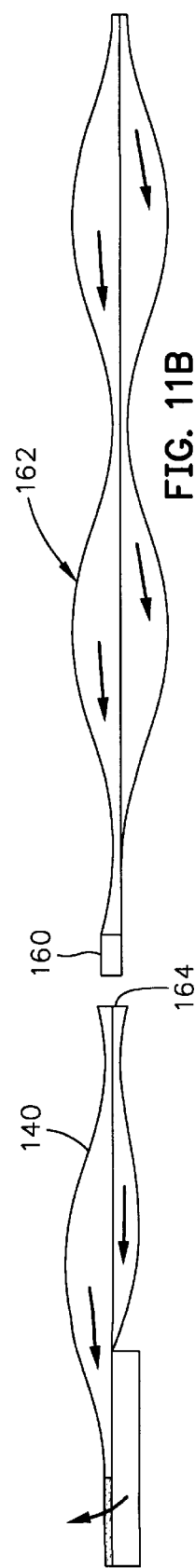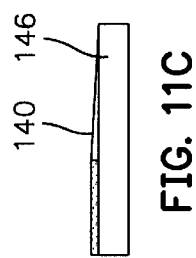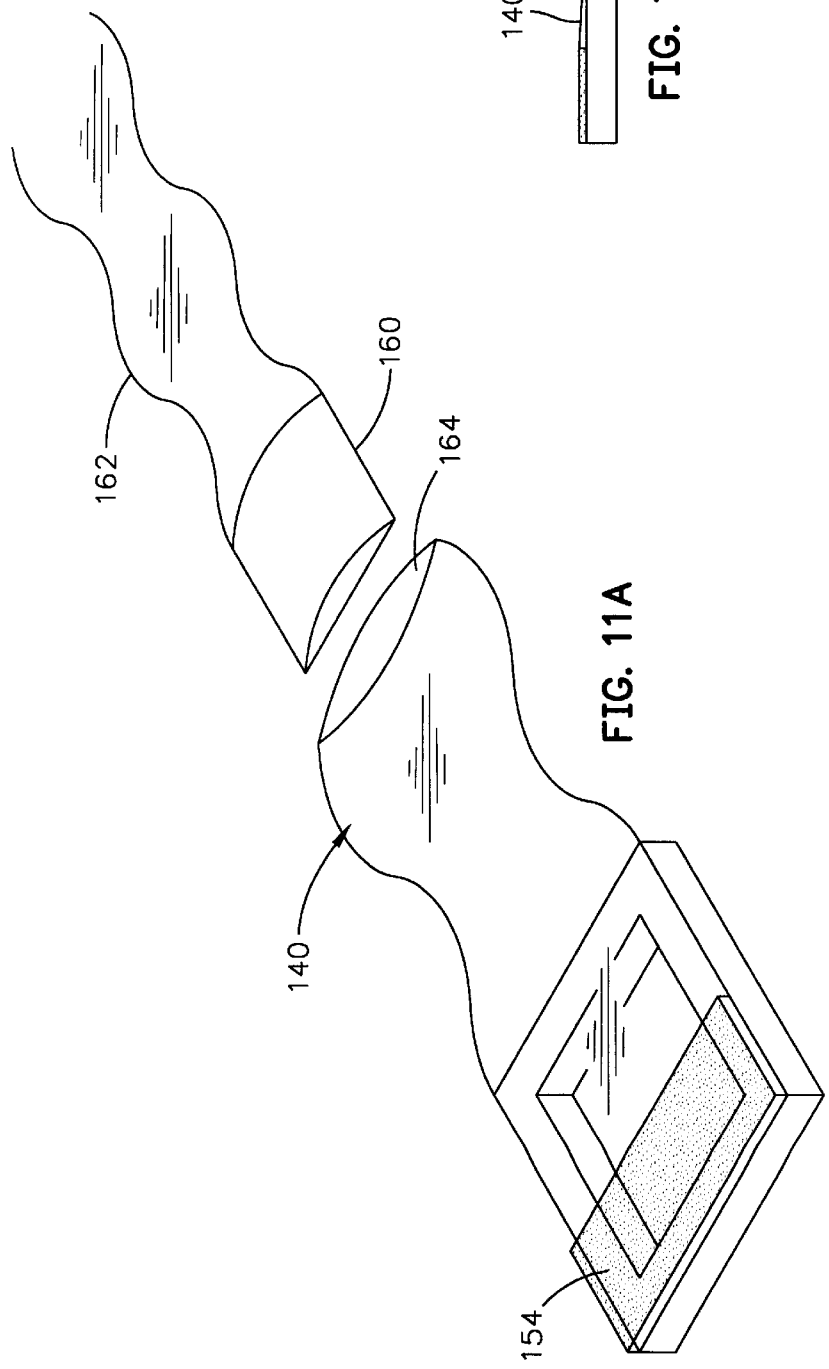

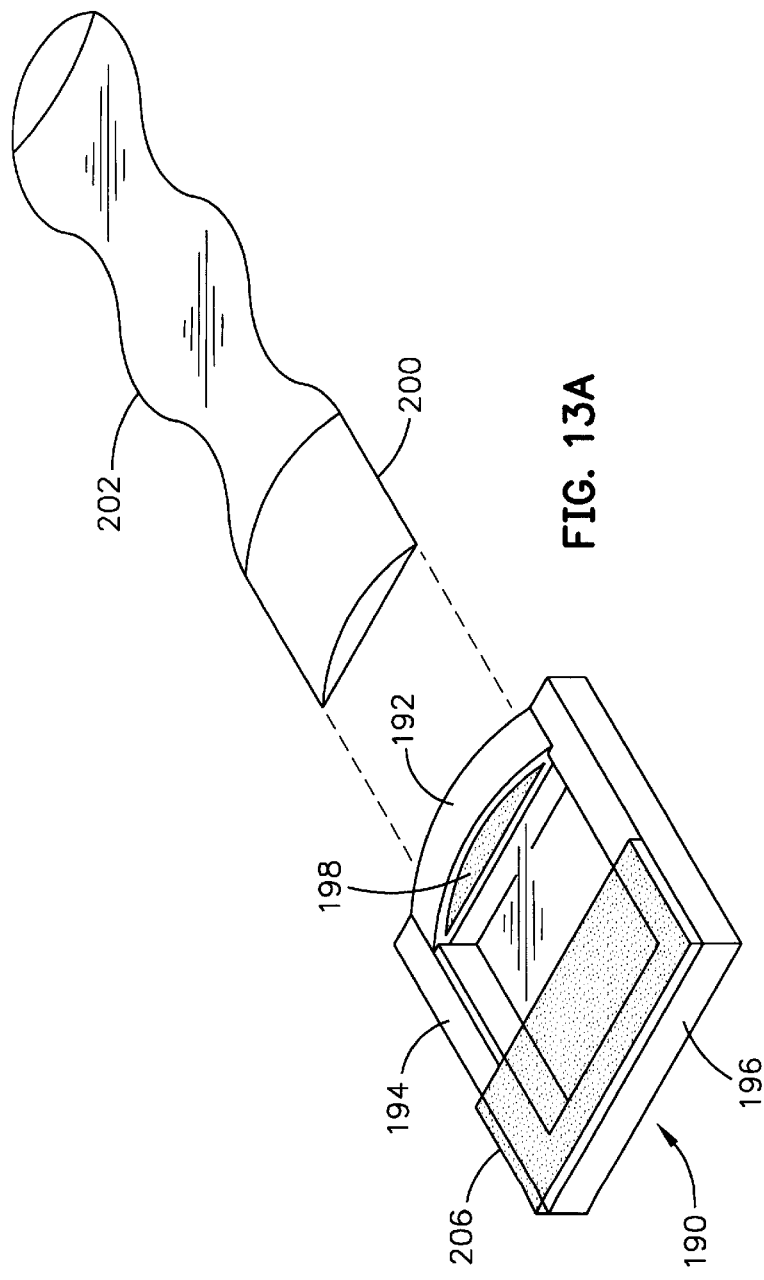
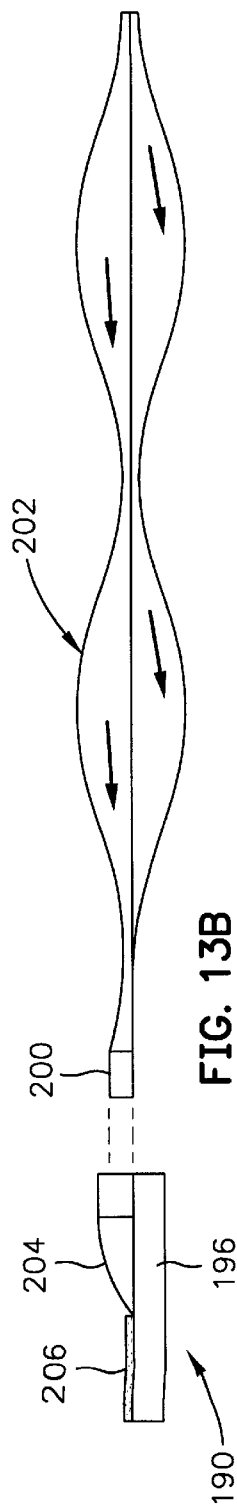
FIG. 13A
FIG. 13B

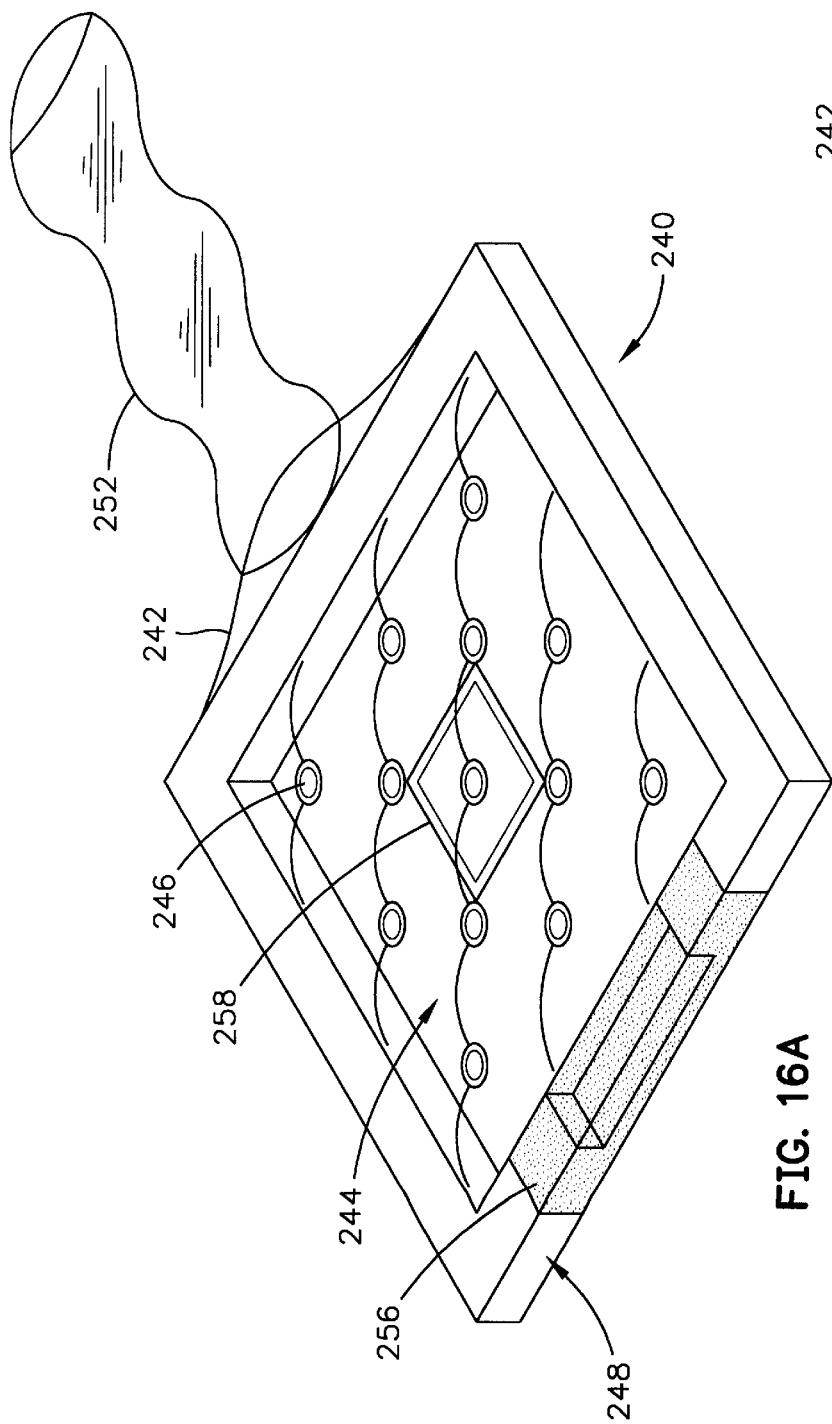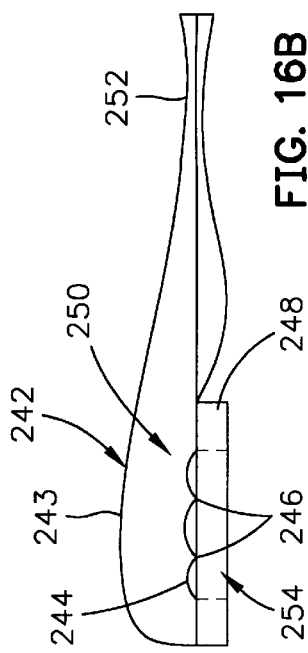
FIG. 16A
FIG. 16B

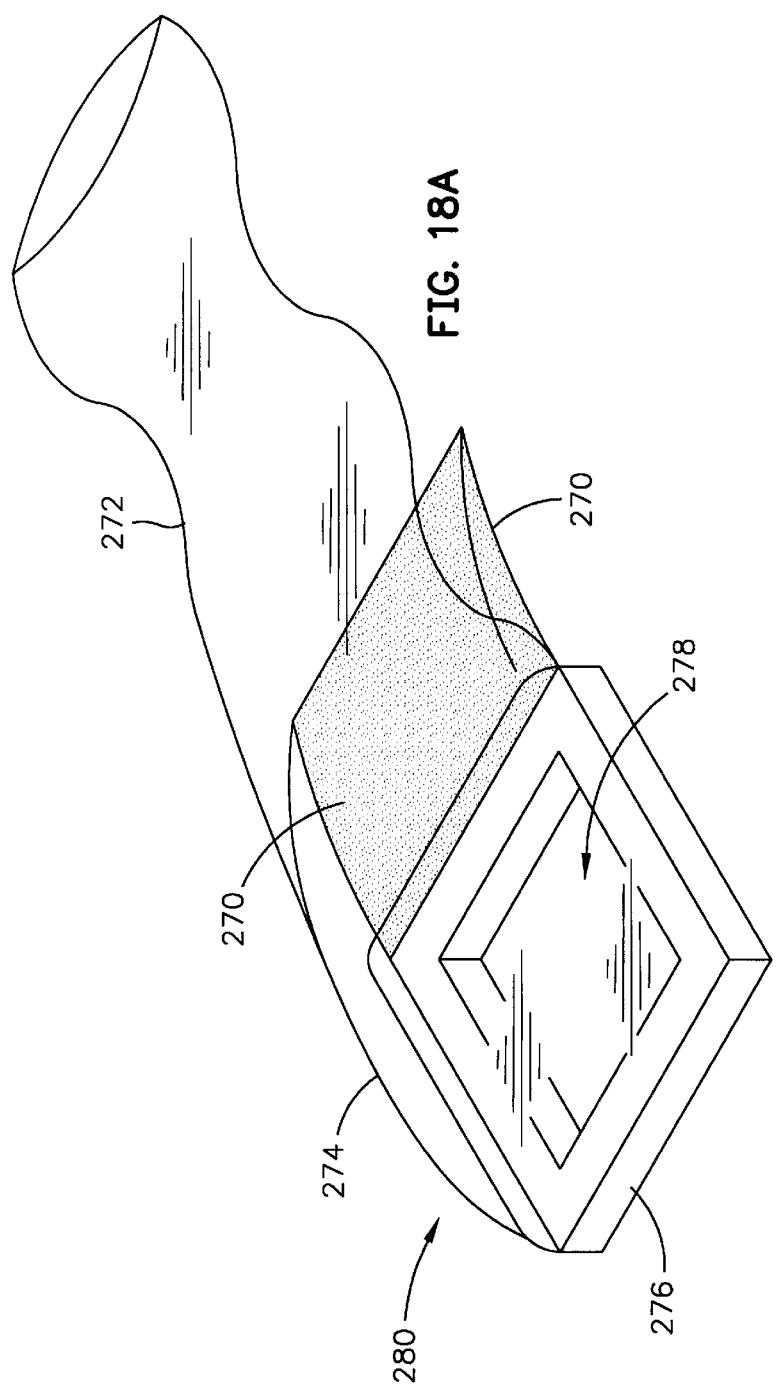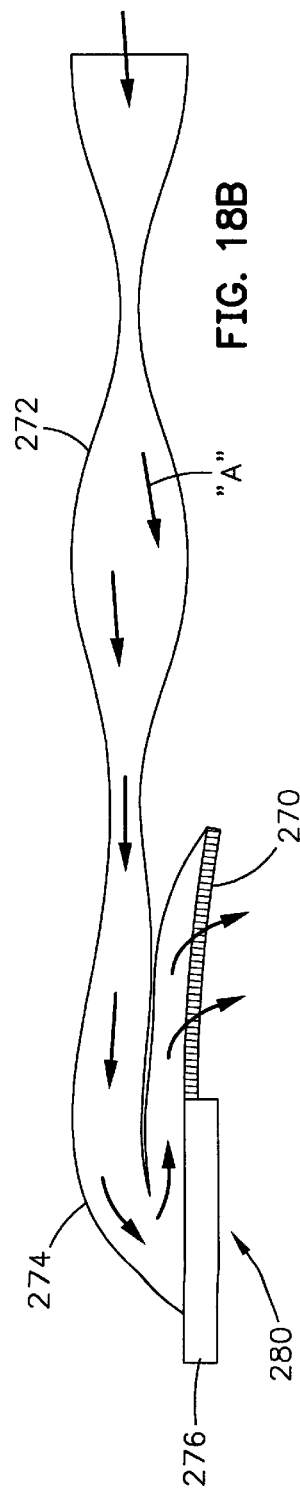
FIG. 18A
FIG. 18B

NORMOTHERMIC TISSUE HEATING WOUND COVERING

CROSS REFERENCES TO RELATED CO-PENDING APPLICATIONS

This application is a continuation-in-part application of U.S. patent application Ser. No. 08/356,325, filed Feb. 21, 1995, titled WOUND COVERING, now abandoned, which is a 35 U.S.C. §371 application of PCT international application Ser. No. PCT/US93/05876, filed Jun. 18, 1993, titled WOUND COVERING which is a continuation-in-part of, and claims priority from, U.S. patent application Ser. No. 07/900,656, filed Jun. 19, 1992 titled THERMAL BODY TREATMENT APPARATUS AND METHOD, now abandoned. This application is related to U.S. patent application Ser. No. 08/785,794, filed Jan. 21, 1997, titled NORMOTHERMIC HEATER WOUND COVERING, U.S. patent application Ser. No. 08/786,714, filed Jan. 21, 1997, titled NEAR HYPERTHERMIC HEATER WOUND COVERING, U.S. patent application Ser. No. 08/342,741, filed Nov. 21, 1994, for WOUND TREATMENT DEVICE, now U.S. Pat. No. 5,817,145, U.S. patent application Ser. No. 08/838,618, filed Apr. 11, 1997, for "FLEXIBLE NON-CONTACT WOUND TREATMENT DEVICE", and U.S. patent application Ser. No. 08/843,072, filed Apr. 11, 1997, for "FLEXIBLE NON-CONTACT WOUND TREATMENT DEVICE WITH A SINGLE JOINT".

FIELD OF THE INVENTION

This invention relates to a wound covering for wound treatment and, in particular, wound covers having a substantial portion of the wound cover in non-contact with the wound and capable of delivering heat to the wound. The wound covering preferably controls the temperature, humidity and other aspects of the environment at the wound site.

BACKGROUND OF THE INVENTION

Wounds in general, as used in this context, are breaks in the integrity of the skin of a patient. Wounds may occur by several different mechanisms. One such mechanism is through mechanical traumatic means such as cuts, tears, and abrasions. There are many instruments of causality for mechanical wounds, including a kitchen bread knife, broken glass, gravel on the street, or a surgeon's scalpel. A different mechanism cause for mechanical wounds is the variable combination of heat and pressure, when the heat alone is insufficient to cause an outright burn. Such wounds that result are collectively referred to as pressure sores, decubitus ulcers, or bed sores, and reflect a mechanical injury that is more chronic in nature.

Another type of mechanism causing a wound is vascular in origin, either arterial or venous. The blood flow through the affected region is altered sufficiently to cause secondary weakening of the tissues which eventually disrupt, forming a wound. In the case of arterial causes, the primary difficulty is getting oxygenated blood to the affected area. For venous causes, the primary difficulty is fluid congestion to the affected area which backs up, decreasing the flow of oxygenated blood. Because these wounds represent the skin manifestation of other underlying chronic disease processes, for example, atherosclerotic vascular disease, congestive heart failure, and diabetes, these vascular injuries also are chronic in nature, forming wounds with ulcerated bases.

Traditional wound coverings, such as bandages, are used to mechanically cover and assist in closing wounds. Such bandages typically cover the wound in direct contact with the wound. This may be acceptable for acute, non-infected traumatic wounds, but it must be kept in mind that direct bandage contact with a wound can interfere with the healing process. This interference is particularly prevalent for chronic ulcerated wounds because of the repeated mechanical impact and interaction of the bandage with the fragile, pressure sensitive tissues within the wound.

The benefits of application of heat to a wound are known, and documented benefits include: increased cutaneous and subcutaneous blood flow; increased oxygen partial pressure at the wound site; and increased immune system functions, both humoral and cell mediated, including increased migration of white blood cells and fibroblasts to the site.

However, heat therapy for the treatment of wounds, either infected or clean, has been difficult to achieve in practice. For instance, heating lamps have been used, but these resulted in drying of wounds, and in some cases, even burning tissue from the high heat. Due to these and other difficulties, and since most acute wounds usually heal over time, physicians no longer consider the application of heat to the wound as part of the treatment process. The thinking among medical personnel is that any interference in a natural process should be minimized until it is probable that the natural process is going to fail. Additionally, the availability of antibiotics for use in association with infected wounds has taken precedence over other therapies for the treatment of chronic wounds and topical infections.

In French patent number 1,527,887 issued Apr. 29, 1968 to Veilhan there is disclosed a covering with a rigid oval dome, its edge resting directly on the patient's skin. One aspect of the Veilhan wound protector is a single oval heating element resting on the outer surface of the rigid dome, positioned at the periphery of the rigid dome. Veilhan does not discuss the heating aspect other than to state that it is a component.

The benefits of controlling other environmental parameters around the wound site are not as well known. Controlling the humidity at the wound site and the benefits of isolating the wound have not been extensively studied and documented.

While the benefit of applying heat to wounds is generally known, the manner of how that heat should be used or applied is not known. Historically, heat was applied at higher temperatures with the goal of making the wound hyperthermic. These higher temperatures often resulted in increasing tissue damage rather than their intended purpose of wound therapy and healing. There is a need for appropriate wound care management incorporating a heating regimen that is conducive to wound healing, yet safe and cost effective.

SUMMARY OF THE INVENTION

The present invention disclosed herein approaches the treatment of wounds with heat based on an understanding of physiology. The normal core temperature of the human body, defined herein for purposes of this disclosure, is 37° C.±1° C. (36–38° C.), which represents the normal range of core temperatures for the human population. For purposes of discussion and this disclosure, normal core temperature is the same as normothermia. Depending on the environmental ambient temperature, insulative clothing and location on the body, skin temperature typically ranges between about 32° C. and about 37° C. From a physiologic point of view, a 32° C. skin temperature of the healthy distal leg is moderate hypothermia. The skin of the distal leg of a patient with vascular insufficiency may be as low as 25° C. under normal conditions, which is severe hypothermia.

A fundamental physiologic premise is that all cellular physiologic functions, biochemical and enzymatic reactions in the human body are optimal at normal body core temperature. The importance of this premise is seen in how tightly core temperature is regulated. Normal thermoregulatory responses occur when the core temperature changes as little as ±0.1° C. However, the skin, as noted above, is usually hypothermic to varying degrees. For example, the skin of the torso is usually only slightly hypothermic, whereas the skin of the lower legs is always hypothermic. Consequently, wounds and ulcers of the skin, regardless of location, are usually hypothermic. This skin hypothermia slows cellular functions and biochemical reactions, inhibiting wound healing.

The effects of hypothermia on healing are well known. A number of regulatory systems within a human are affected, such as the immune system and coagulation, with both platelet function as well as the clotting cascade affected. Patients with hypothermic wounds experience more infections which are more difficult to treat, have increased bleeding times and have been shown to require more transfusions of blood. All of these complications increase morbidity and the cost of patient care and, to a lesser extent, increase the likelihood of mortality.

One purpose of the present invention is to raise the wound tissue and/or periwound tissue temperatures toward normothermia to promote a more optimal healing environment. The present invention is not a "heating therapy", per se, where it is the intent of "heating therapy" to heat the tissue above normothermia to hyperthermia levels. Rather, the present invention is intended to bring the wound and periwound tissues toward normothermia without exceeding normothermia.

The medical community has not historically considered normothermic heating to be therapeutic. Many physicians feel that hypothermia is protective and, therefore, desirable. Studies with the present invention would indicate that this widely held belief that hypothermia is at least benign or possibly beneficial is incorrect with regard to wound healing.

The present invention is a wound covering for application to a selected treatment area of a patient's body that includes, at least as a portion of the selected treatment area, a target tissue of a selected wound area. The selected treatment area may also include a portion of the area immediately proximate to the wound area referred to as the periwound area. The wound covering comprises a heater suitable for providing heat to at least a portion of the selected treatment area, an attachment for attaching the heater in a non-contact position proximate the selected treatment area, a heater controller, connected to the heater and including a power source for the heater, for controlling the heater, and an input control to the heater controller providing guidance to the heater controller so as to heat the wound and/or periwound tissue to a temperature in a range from a pretreatment temperature to about 38° C. Pretreatment temperature is that temperature the wound tissue is at when therapy begins and is usually somewhat above ambient temperature and also is variably dependent on where the wound is located on a patient's body skin surface. The ambient temperature is that temperature of the environment immediately around the selected treatment area not a part of the patient's body, i.e., the bed, the air in the room, the patient's clothing.

The heater is selectable from among several types of heat sources such as warmed gases directed over the selected treatment area and electrical heater arrays placed proximate the selected treatment area. Electrical heater arrays are adaptable for construction into a layer of variable proportion and geometry or as a point source. The present invention anticipates the ability to provide several different sizes and geometric configurations for the heater. The present invention is flexible in being able to provide uniform heating over the entire selected treatment area or provide a non-uniform heating distribution over selected portions of the selected treatment area. Alternate heat source embodiments could include warm water pads, exothermic chemical heating pads, phase-change salt pads, or other heat source materials.

The present invention anticipates that the controller is able to control both the temperature and the duration of the application of heat. This control may extend from manual to fully automatic. Manual control anticipates the controller maintaining the heater temperature at an operator-selected temperature for as long as the operator leaves the heater on. More automatic modes provide the operator an ability to enter duty cycles, to set operating temperatures, as well as to define therapy cycles and therapeutic sequences. As used herein, a duty cycle is a single on cycle when heating of the heater is occurring, measured from the beginning of the on cycle to the end of that on cycle. A heater cycle is a single complete on/off cycle measured from the beginning of a duty cycle to the beginning of the next duty cycle. Consequently, a duty cycle may also be represented in a percentage of or as a ratio of the time on over the time off. A plurality of heater cycles are used to maintain heater temperature around a selectable temperature set point during a therapy cycle which is defined as an "on" period, composed of a plurality of heater cycles, and an "off" period equivalent to remaining off for an extended period of time. A therapeutic sequence, as used herein, is a longer period of time usually involving a plurality of therapy cycles spread out over an extended period of time, the most obvious being a day in length. The present invention anticipates the use of any period of time as a therapeutic sequence and involving one, or more than one therapy cycles.

The present invention also anticipates programmability for a number of modalities including peak heater temperature for a duty cycle and/or therapy cycle, average heater temperature for a duty cycle and/or therapy cycle, minimum heater temperature for a heater cycle and/or therapy cycle, ratio of duty cycle, length of therapy cycle, number of duty cycles within a therapy cycle, and number of therapy cycles in a therapeutic sequence. Different duty cycles within a therapy cycle may be programmed to have different peak heater temperatures and/or heater cycles may have average heater temperatures over that therapy cycle. Different therapy cycles within a therapeutic sequence may be programmed to have different peak heater temperatures and/or average heater temperatures over each therapy cycle. The wound covering control is operator-programmable or may have preprogrammed duty cycles, therapy cycles, and therapeutic sequences selectable by the operator.

The input control may take several forms. One form of input control is a temperature feedback from a temperature sensor placed proximate the selected area of treatment to monitor the target tissue temperature response. The sensor provides to the input control, a sequence of temperature values for the target tissue of the selected treatment area. Programmability may provide for variable heater output dependent on the actual target tissue temperature as well as the rate of target tissue temperature change within the selected treatment area.

Another form of input control is for the controller of the present invention to follow a temperature treatment paradigm programmable within the controller which is based on one or more parameters derived empirically, such as: the thermodynamic characteristic of tissue, the heat conduction rate of tissue types, the wound location, the wound type, the wound stage, the wound blood flow, the tissue surface area involved in the selected treatment area, the tissue volume involved in the selected treatment area, the heater geometry, the heater output, the heater surface area, and the ambient temperature. This paradigm programming provides an operator the ability, when selecting a treatment mode or method, to take into account all of these parameters. More importantly, the operator is able to tailor a treatment mode based on the type of wound to be treated. For example, wound types, such as wounds secondary to arterial insufficiency versus those secondary to venous insufficiency, or the location of the tissue on the body, for example, the leg versus the sacrum or abdomen, are sufficiently different so as to necessitate different heater treatment methods that take into account the myriad number of differences between wound types. One or more parameters are inputted to the controller to provide a sequence of target tissue temperatures over time to the heater controller based on the parameters used.

A preferred form of the wound covering includes an attachment as a peripheral sealing ring which, in use, completely surrounds the area of the wound and periwound, i.e., the selected treatment area. The upper surface of the peripheral sealing ring is spanned by a continuous layer which is preferably transparent and substantially impermeable, although the present invention also anticipates the use of a gas permeable layer suitable for some applications. Once in position, the sealing ring and the layer define a wound treatment volume which surrounds the wound. Additionally, the layer spanning the peripheral sealing ring may be sealed about the periphery of the sealing ring and act as a barrier layer over the wound treatment volume. Optionally, the heater may be incorporated into the barrier layer or the barrier layer may be incorporated into the heater. An adhesive and a suitable release liner is applied to the lower surface of the peripheral sealing ring to facilitate the application of the wound covering to the patient's skin.

The barrier layer may include a pocket adapted to receive an active heater. An alternate form of the invention provides for the transport of heated air from a remote heat source to the wound treatment volume. In the active heater embodiments a thermostat and/or a pressure-activated switch may be used to control the heating effects of the heater. Passively heated embodiments are contemplated as well. These passive versions of the device include the use of thermally insulating coverings which retain body heat within the treatment volume. These reflectors or insulators may be placed in a pocket formed in the barrier layer. Each of these heated embodiments promote wound healing by maintaining the wound site at a generally elevated, but controlled, temperature.

In general, the peripheral sealing ring is made from an absorbent material which may act as a reservoir to retain and/or dispense moisture into the treatment volume increasing the humidity at the wound site. The reservoir may also contain and deliver medicaments and the like to promote healing.

The present invention is designed to directly elevate the temperature of the hypothermic skin and subcutaneous tissue of the selected wound area to a temperature which is close to or at normothermia. The purpose of this device is to create within the wound and periwound tissues of the selected treatment area a more normal physiologic condition, specifically a more normothermic condition, which is conducive to better wound healing. The present invention anticipates the use of an active heater that creates a heat gradient from heater to wound and periwound tissues. The usual temperature gradient for tissues goes from about 37° C. deep in the body core down to about 320 C. at the skin surface of the leg. The heater of the present invention operates in an output range suitable to raise the temperature of the selected treatment tissue from its pretreatment temperature to not more than 38° C.

In contrast, typical local heating therapy (e.g. hot water bottles, hot water pads, chemical warmers, infrared lamps) deliver temperatures greater than 46° C. to the skin. The goal of traditional heating therapy is to heat the tissue above normal, to hyperthermic temperatures.

The present invention differs from infrared lamps in two ways. First, the present invention includes a dome over the wound that is relatively impermeable to water vapor transmission. After application of the bandage, moisture from the intact skin or wound evaporates, and air within the dome quickly reaches 100% relative humidity. The interior of the present invention is now warm and humid. For example, a 2.5 square inch bandage at 28° C. requires only 0.0014 g of water to reach saturation. When the air is thus saturated, no further evaporation can occur and, therefore, no drying of the wound can occur. This equilibrium will be maintained as long as the bandage is attached to the patient.

When heat is provided by the preferred embodiment of the present invention, the absolute amount of water needed to reach 100% relative humidity is slightly increased since warm air has a greater capacity for holding moisture. However, the air within the dome of the bandage still reaches water vapor saturation very quickly, and no further evaporation occurs. For example, a 2.5 square inch bandage of the present invention at 38° C. requires only 0.0024 g of water to reach saturation. Excess moisture is absorbed by the foam ring, but still is retained within the bandage. The enclosed dome design maintains 100% humidity over the wound which also prevents evaporation due to the heat. As long as the humidity is retained within the bandage, heating therapy could theoretically be continued indefinitely without causing the wound to dry. In contrast, when using infrared lamps, the wounds are open and exposed to the environment. The result is excessive drying of the wound, increasing tissue damage.

Secondly, the present invention operates at low temperatures, from above ambient to about 38° C. This causes only minimal heating of the skin. In contrast, infrared lamps operate at temperatures in excess of 200° C. These lamps heat the wound to hyperthermic temperatures which can cause thermal damage to the tissue of the wound.

At the low (normothermic) operating temperatures of the present invention, the heat transfer to the skin is minimal. The low wattage heater, the inefficiencies of the heat transfer into the tissue, the thermal mass of the tissue and the blood flow (even if markedly reduced), all prevent the wound temperature from reaching the heater temperature. Hypothermic wound tissue is warmed as a result of "migration" of the body's core temperature zone toward the local wound area.

The following data document the tissue temperatures resulting from a 38° C. heater of the present invention on:

|                                  | Average | Maximum |
| -------------------------------- | ------- | ------- |
| Normally perfused human skin     | 36° C.  | 36° C.  |
| Arterial/diabetic foot ulcers    | 32° C.  | 35° C.  |
| Venous/arterial leg/foot ulcers  | 33° C.  | 35° C.  |
| Non-perfused human model         | 35° C.  | 35° C.  |

When warmed with a 38° C. heater, wounds on poorly perfused legs reach stable average temperatures of 32–33° C. In contrast, normally perfused skin reaches 36°C. It is important to note that these data are contradictory to the assumption that poorly perfused tissue would reach a higher temperature than normally perfused tissue. This result substantiates the physiologic finding that the "migration" of the core temperature zone toward the local wound zone, decreasing the gradient difference between the core and surface temperatures, is the cause for the observed increased wound temperatures. Core temperature regulation is heavily dependent on perfusion, and migration of the core temperature zone is also heavily dependent on perfusion. At no point in time did the poorly perfused tissue reach normothermia. Consequently, poorly perfused legs are much colder than normally perfused legs, and, thus, poorly perfused legs constitute a substantially deeper heat-sink.

A wound-healing pilot study is under way, studying patients with chronic arterial and/or venous ulcers of the lower leg. These patients have suffered from these ulcers for many months and, in some cases, even years, despite aggressive medical and surgical therapy. Of 29 patients enrolled, 24 have completed the study protocol or are still being treated. Of these 24 patients, 29% are completely healed, and 38% show a significant reduction of the wound size within 2–5 weeks of receiving therapy with the present invention.

A known consequence of restoring normothermia to tissues is to induce some degree of vasodilatation which increases local blood flow. Preliminary data collected during trials of the present invention, studying the effects of the present invention on normal subjects and on wound healing, has borne this out. An added effect has been to increase the partial pressure of oxygen in the subcutaneous tissues ($P_{sq}O_2$), which is an indirect indicator of the status of the tissue. The higher the $P_{sq}O_2$, the greater the likelihood the tissue will benefit and improve the healing process. The results of some of these studies are presented in Tables 1–4.

In conducting the studies presented in Tables 1–4, a wound covering according to the present invention is placed over the skin. The temperature of the subcutaneous tissue is then measured over time. From −60 minutes to the 0 minute mark, the heater is off in order to obtain a baseline temperature. At the 0 minute mark the heater is activated and its temperature kept constant over the next 120 minutes when it is turned off. Temperature measurements were taken during this 120 minute period and for an additional 180 minutes after turning the heater off. As shown in Table 1, with activation of the heater to 38° C., the subcutaneous tissue temperature rapidly rose from about 34.3° C. to about 36° C. over the first 30 minutes. The temperature of the subcutaneous tissue continued to slowly raise over the next 90 minutes to a temperature of about 36.7° C. After turning the heater off, the temperature of the subcutaneous tissue fell to about 35.9° C. and held this temperature fairly uniformly for at least the next 120 minutes.

Table 2 presents the skin temperature data collected from within the wound cover of the present invention for the same periods as those in Table 1. The general curve shape is similar to the subcutaneous tissue temperature curve. The baseline temperature at the 0 minute mark was about 33.5° C. After turning the heater on to 38° C., the skin temperature rose rapidly to about 35.8° C. in the first 30 minutes, then slowly rose to about 36.2° C. by the end of the 120 minute heating period. After turing the heater off, the skin temperature fell to about 35° C. and held there for at least the next two hours.

Table 3 represents laser Doppler data collected from the tissue during the experiments and correlates to blood flow through the local area being treated with heat. The baseline flow is approximately 80 ml/100 g/min and rises to about 200 ml/100 g/min at its peak, half way through the heating period. The flow "normalizes" back to baseline during the last half of the heating period and remains at about baseline for the remainder of the measuring period.

The change in $P_{sq}O_2$ is followed in Table 4. The baseline $P_{sq}O_2$ is about 75 when heating begins and rises steadily to about 130 by the end of the heating period. The $P_{sq}O_2$ remains at this level for the remainder of the measuring period despite the lack of heating for the last 180 minutes. The added benefit of increased $P_{sq}O_2$ by heating continues well into the period of time after active heating has ceased. Wounds will continue to benefit from the effects of heating for substantial periods of time after the heating is turned off. The consequences of this study with the present invention is that the heating need not be constant, but deliverable over a heater therapy cycle or cycles that may or may not be part of a larger therapeutic sequence.

Similar trials were conducted using a heater temperature of 46° C. This data is presented in tables 5–8. Only slight additional benefits were found in any of the four measured parameters when studied at this higher temperature. The benefits imparted by active heating according to the present invention seem to peak at about 46° C. In many instances, 43° C. appears to be the optimal temperature for maximal efficiency in terms of least energy required for the greatest therapeutic gain.

Our initial human clinical data shows that the beneficial effects of heating on blood flow and $P_{sq}O_2$ last at least one hour longer than the actual duration of heat application. Further, we have noted that cycled heating seems to be more effective for wound healing than continuous heating. Therefore, the data recommends cycling the heater in a therapy cycle (e.g. 1 hour "on" and 1 hour "off") for a total heating time of 2–8 hours per day as a therapeutic sequence.

None of the 29 patients with compromised circulation treated to date have shown any indication of skin damage due to 38° C. heat. Furthermore, none of these wounds have exceeded 35° C. tissue temperature, with an average wound temperature of 32–33° C. The present invention raises the wound temperature toward normothermia, but even on a poorly perfused leg, the tissue does not reach normothermia.

BRIEF DESCRIPTION OF THE DRAWINGS

Illustrative but not limiting embodiments of the invention are shown in the attached drawings. Throughout the several figures like reference numerals refer to identical structure throughout, in which:

FIG. 8A is an exploded view of an alternate wound covering:

FIG. 8B is an assembly view showing the air flow through the wound covering;

FIG. 9A is a perspective view of an alternate wound covering;

FIG. 9B is a side view of the wound covering of FIG. 9A;

FIG. 10 is a perspective view of an alternate wound covering;

FIG. 11A is a perspective view of an alternate wound covering;

FIG. 11B is a side elevational view of the wound covering of FIG. 11A;

FIG. 11C is a view of the wound covering of FIG. 11A;

FIG. 13A is an alternate connector arrangement for the wound covering;

FIG. 13B is a side sectional view of the wound covering of FIG. 13A;

FIG. 16A is a view of a two ply barrier layer wound covering;

FIG. 16B is a side elevational view of the wound covering of FIG. 16A;

FIG. 18A is an alternate wound covering;

FIG. 18B is a side sectional view of the wound covering of FIG. 18A;

DETAILED DESCRIPTION OF THE INVENTION

The present invention is directed to a non-contact wound covering for controlling the local environment at a wound site on a patient. A wound site includes those portions of the patient's skin obviously definable as the wound area and the immediately adjacent periwound area as the selected treatment area of the wound site. The wound covering protects the wound from contamination by materials from the outside environment and also prevents the wound site from shedding contaminants into the local environment of the patient, i.e. the hospital room. The treatment volume formed proximate the wound site can be controlled to create an optimal healing environment. The word "wound" as used herein refers generically to surgical incisions, ulcers, or other lesions or breaks in the skin.

First, a substantially vertical wall is provided to encircle the selected treatment area on the surface of the patient's skin. This vertical wall provides an upper surface to support a layer spanning this structure above the level of the wound and a lower surface suitable for attachment to the patient's skin. This structure is referred to throughout as an attachment or a peripheral sealing ring. Together these elements form a wound treatment volume between the layer and the surface of the selected treatment area. The fact that the layer does not contact the wound itself promotes healing by minimizing mechanical stresses on the tissues. The lower surface suitable for attaching to the skin may include an adhesive and a complimentary release liner assembly to facilitate the attachment of the wound covering to the skin of the patient. The present invention anticipates using a heater such that the layer may comprise the heater formed as the layer or as a layer which includes a heater within some portion of the layer. The layer may also include functioning as a barrier layer completely enclosing the wound treatment volume.

In accordance with the present invention, the climate within the wound treatment volume may be controlled. Typically the temperature, humidity, and gas composition, for example adding oxygen, nitric oxide or ozone, are controlled. Also, aerosolized medications or compounds may be released into this volume as well. The above list is exemplary of the climate controls which may promote healing of the wound, and is not intended to limit the scope of the present invention. It will be understood by those skilled in the art that numerous other climate factors can be controlled within the treatment volume of the present wound covering system without departing from the scope of the invention.

Figure 1A:
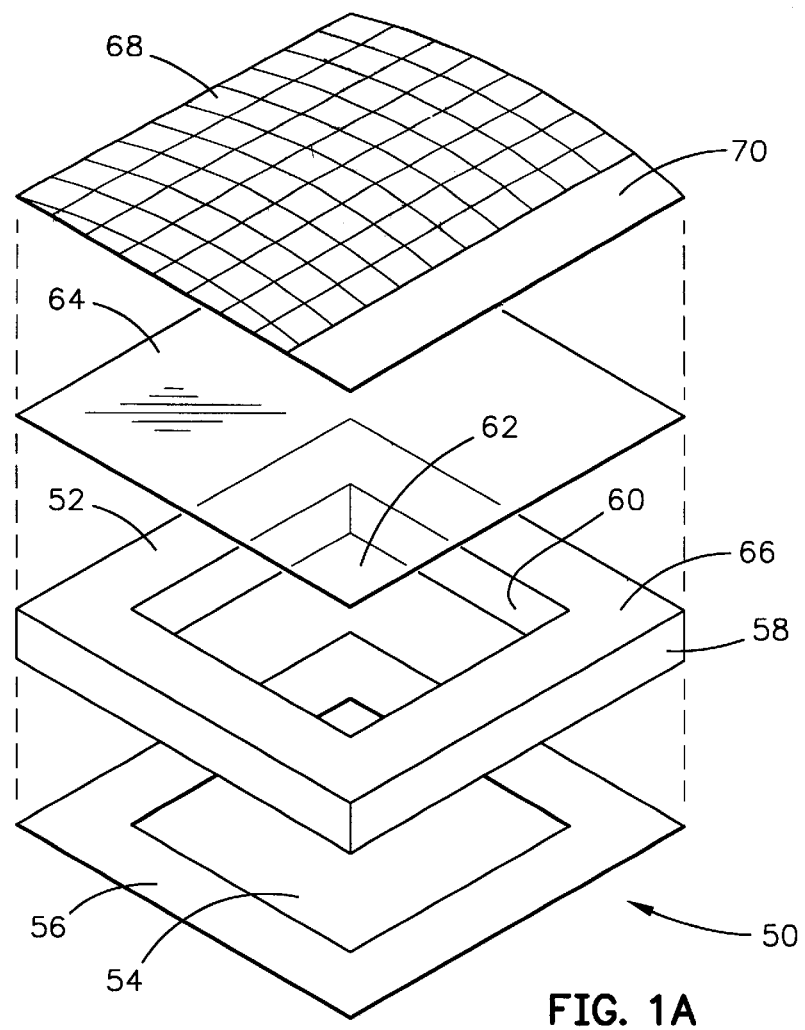
FIG. 1A is an exploded view of a wound covering according to the present invention.

FIG. 1A illustrates an exploded view of a wound covering 50. In this embodiment, a peripheral sealing ring 52 is substantially square in outline. Peripheral sealing ring 52 is intended to be attached to uninjured skin surrounding a selected treatment area 54 using an adhesive 56. In this embodiment, a layer of adhesive hydrogel is shown as the adhesive 56. Additionally, peripheral sealing ring 52 is preferably constructed of an open cell hydrophilic foam plastic having a sealed outer surface 58 which isolates the wound from the environment. The peripheral sealing ring is fabricated from a material which may conform to the curved surface of the patient's body. An inner surface 60 of sealing ring 52 is preferably porous or absorbent so that it can form a reservoir to contain and release moisture or water vapor into the air within a treatment volume 62 to create a high humidity environment if desired. Additionally, the hydrophilic absorbent nature of peripheral sealing ring 52 absorbs fluids and blood weeping from the wound.

A layer 64 is preferably attached to an upper surface 66 of peripheral sealing ring 52 as a barrier layer to seal treatment volume 62. Layer 64 is preferably constructed of a flexible synthetic polymeric film, such as polyethylene, polyvinyl chloride, polyurethane, or polypropylene. Additionally, other polymeric films, natural and semi-synthetic, that are suitable for use in medical applications such as cellulose and cellulose acetate, may be used. A wound tracing grid 68, also constructed of a substantially clear flexible material, may optionally be used as, or attached to, layer 64 to facilitate wound care management so that the physician can draw an outline of the wound as an aid to tracking the healing process of the wound. The wound tracing grid preferably contains a labeling area 70 for identifying the patient, date when the wound was traced, and other patient medical data.

It will be understood by those skilled in the art that the volume of peripheral sealing ring 52 will depend on the structural strength of the support material and the amount of fluid absorption desired. Additionally, the total area of peripheral sealing ring 52 is dependent on the size of the wound. For example, larger wounds and more flexible covers will require a thicker sealing ring so that the center of the cover does not touch the wound.

Figure 1B:
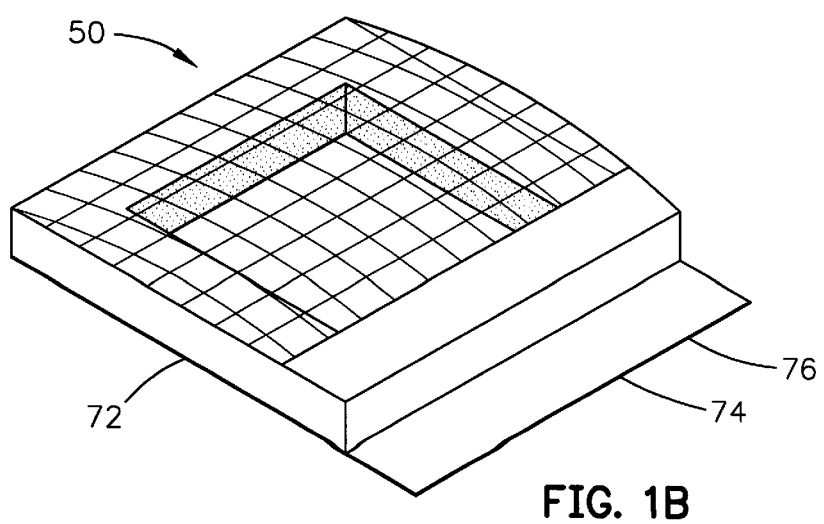
FIG. 1B illustrates an assembled view of the wound covering of FIG. 1A.

Upper surface 66 of peripheral sealing ring 52 is preferably sealed by extending barrier layer 64 over the entire area of upper surface 66 as shown in FIGS. 1A and 1B. Adhesive 56 for attaching peripheral sealing ring 52 to uninjured skin surrounding selected treatment area 54 may take any form, however, the preferred adhesive is preferably a two-faced hydrogel which attaches to a lower surface 72 of peripheral sealing ring 52. This adhesive 56 permits the attachment of peripheral sealing ring 52 to the patient's skin. Finally, peripheral sealing ring 52 may serve as a reservoir for retaining water or medicaments in treatment volume 62 in order to maintain a high humidity in the air within the volume. Water may be added to peripheral sealing ring 52 at any time during treatment.

It will be understood by those skilled in the art that peripheral sealing ring 52 can be supplied in a variety of shapes and sizes to accommodate various wounds. The shapes may include circles, squares, or rectangles. Although it is preferred to dispense the wound covering as a unitary assembly it should be apparent that individual segments of peripheral ring material could be assembled into any shape necessary to form a perimeter around the wound area. Likewise, barrier layer 64 and wound tracing grid 68 could be provided in large sheets which may be cut to size and then attached to the peripheral sealing ring.

FIG. 1B is an assembled view of wound covering 50 of FIG. 1A. To dispense the assembled product, a release liner 74 of FIG. 1B is applied to adhesive 56 in FIG. 1A. Release liner 74 may span the entire lower surface of the covering to maintain the sterility of treatment volume 62. Release liner 74 preferably has a grip tab 76 to facilitate removal of release liner 74 from wound covering 50 immediately prior to application of wound covering 50 to the skin of a patient.

Figure 2A:
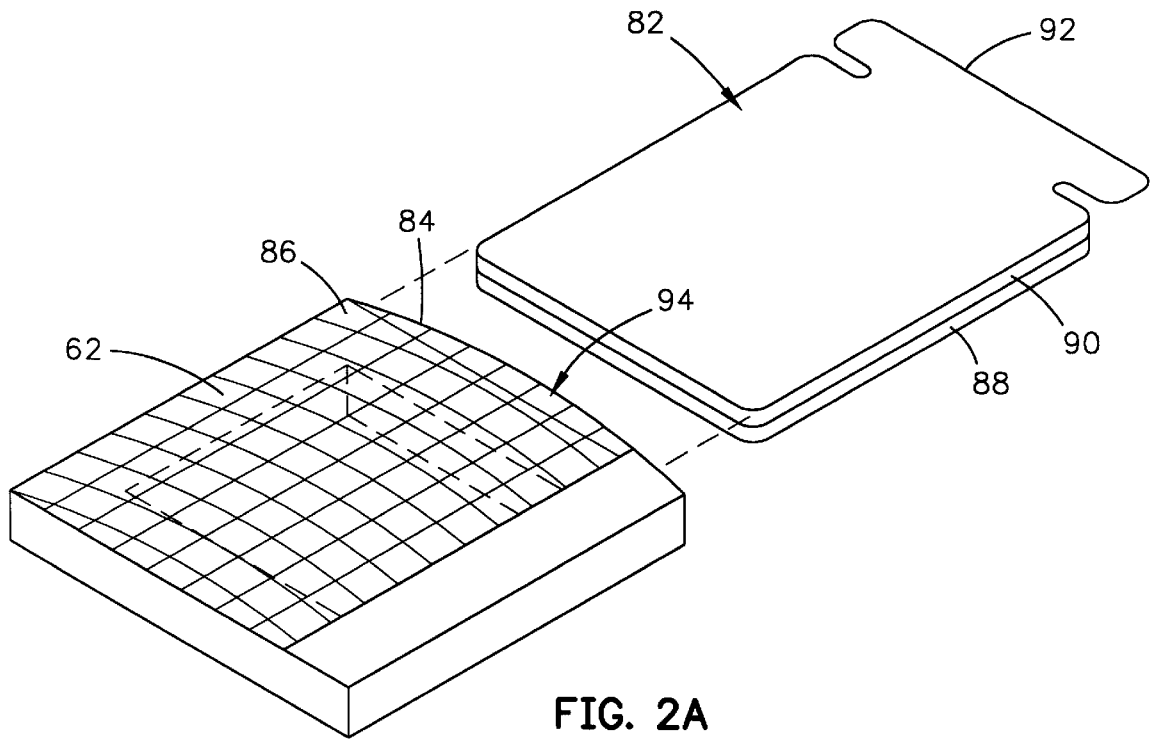
FIG. 2A is a view of an alternate wound covering.
Figure 2B:
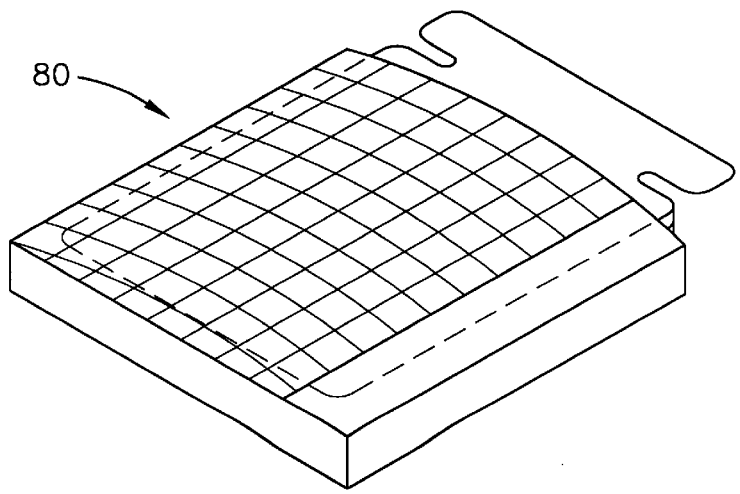
FIG. 2B is a view of an alternate wound covering of FIG. 2A with passive heating card inserted in the wound covering.

FIGS. 2A and 2B illustrate an alternate embodiment of the present invention as a wound covering 80 utilizing passive heating of the treatment volume 62. Because heat is constantly being radiated from the patient's skin surface, the insulation properties of the trapped air within treatment volume 62 will reduce this heat loss. By adding an infrared reflector 82 over treatment volume 62, the infrared heat from the body can be reflected back to the skin for added passive heating.

An edge 84 of wound tracing grid 86 is preferably not attached to the barrier layer to form an envelope or a pocket 94 between the wound tracing grid 86 and the barrier layer. A piece of reflective foil material 88 may be inserted into pocket 94. A thin layer of insulating material 90 may be optionally attached to foil layer 88 to enhance heat retention and to provide foil layer 88 with additional resiliency. A tab 92 is preferably attached to infrared reflector 82 to allow easy insertion and removal from pocket 94 and wound covering 80.

Figure 3A:
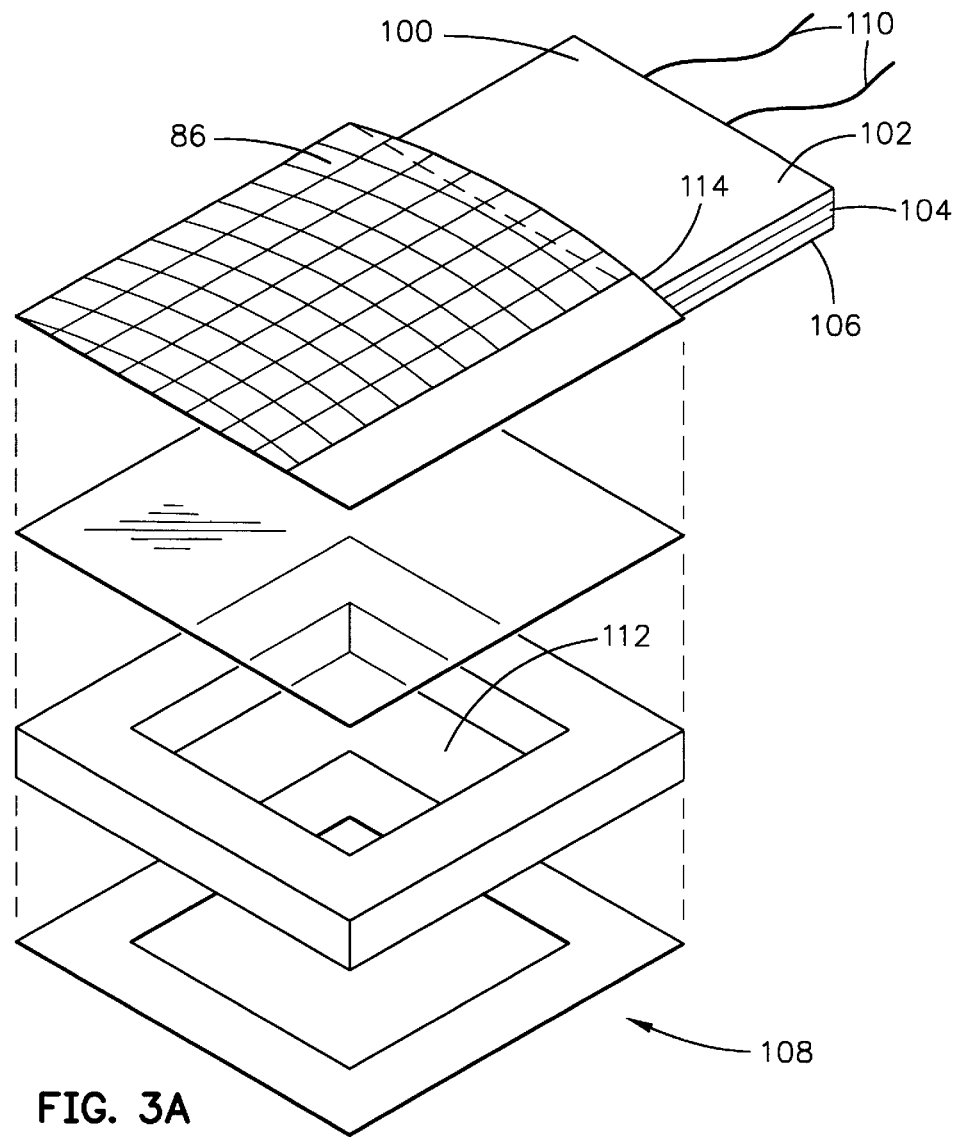
FIG. 3A is an exploded view of an additional alternate wound covering.
Figure 3B:
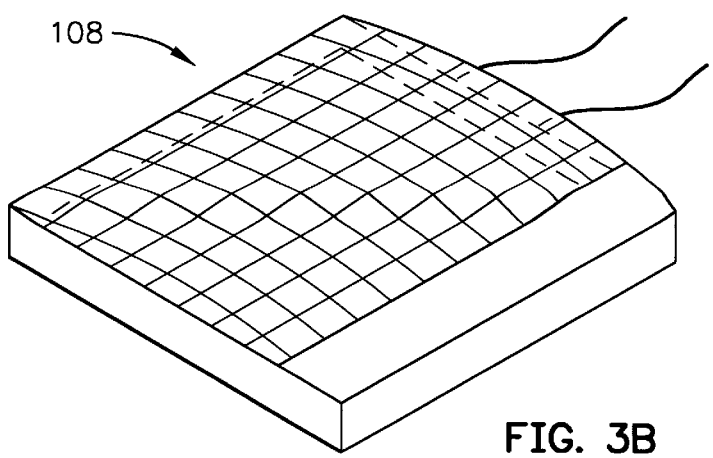
FIG. 3B is an assembled view of the wound covering of FIG. 3A.

FIGS. 3A and 3B illustrate a preferred alternate embodiment of a non-contact wound covering 108 utilizing active heating of a treatment volume 112. Wounds may be safely and easily heated utilizing a heater assembly 100. Heater assembly 100 alternatively comprises a pressure-sensitive switch 102, an insulating layer 104, and a foil heater 106.

Pressure-sensitive switch 102 is optionally laminated to the upper surface of heater assembly 100. The purpose of switch 102 is to shut off power to foil heater 106 in the event that external pressure is applied to wound covering 108 with sufficient force to cause foil heater 106 to contact the skin or wound below. This feature prevents the possibility of applying heat and pressure to the skin at the same time. The combination of heat and pressure is known to cause burns even at low temperatures (40° C.) because the pressure prevents blood flow in the skin making it susceptible to thermal injury. Pressure-sensitive switch 102 preferably covers the entire area of heater assembly 100 so that pressure applied anywhere to the surface of heater assembly 100 will deactivate foil heater 106.

It will be understood by those skilled in the art that a variety of devices are suitable for use as pressure-sensitive switch 102. Force sensing resistors, resembling a membrane switch, which change resistance inversely with applied force are one such example of a pressure sensitive switch. Devices of this type offer the substantial advantage of being low cost, flexible, and durable. A variety of other force sensing switch devices may be utilized as well.

An alternative safety feature anticipated by the present invention is a monitoring function for detecting dramatic increases in power utilization by the heater trying to maintain an operating temperature. Under normal operation, the heater is in a non-contact position proximate the selected treatment area and the heater will have been programmed to operate at a temperature that may be either a straight temperature value or an averaged value for either a duty cycle, therapy cycle or therapeutic sequence. If physical pressure is placed on the heater and it comes into contact with the patient's body, there will be a considerable increase in the rate of heat loss from the heater because of the body's greater heat sink capacity. The heater controller would sense this drop in temperature and initially adjust either the duty cycle ratio or power output, or both, in an attempt to compensate for the increase rate of loss. The safety aspect of this monitoring function would be to override this increase and turn off the device, thus preventing heating the tissue while in direct contact with, and under pressure from, the heater.

Heater element 106 is preferably a thin film type resistance heater which is commercially available. Such thin film resistance heaters utilize low voltage, minimizing the electrical risk to the patient and allowing for battery-powered mobility. Foil heater 106 is preferably sized for each wound covering 108. In actual use, foil heater 106 is preferably provided in sheets with a pair of electrical leads 110 along one edge. While an electrical resistance heater is the preferred embodiment of the invention, other heating devices are anticipated such as warm water pads, exothermic chemical heating pads, and phase-change salt pads.

Heater assembly 100 is preferably insertable into a pocket 114 formed between wound tracing grid 86 and the barrier layer as discussed above. Finally, a temperature monitoring device, such as a liquid crystal temperature monitor, may be applied to an upper surface of heater assembly 100 or within treatment volume 112 to monitor the temperature within treatment volume 112.

FIGS. 4–7 illustrate an alternate embodiment of wound covering 10. In this embodiment, wound covering 10 includes a generally circular head, designated generally at 12, which transitions to an elongated non-kinking, collapsible air supply or hose 14.

Figure 4:
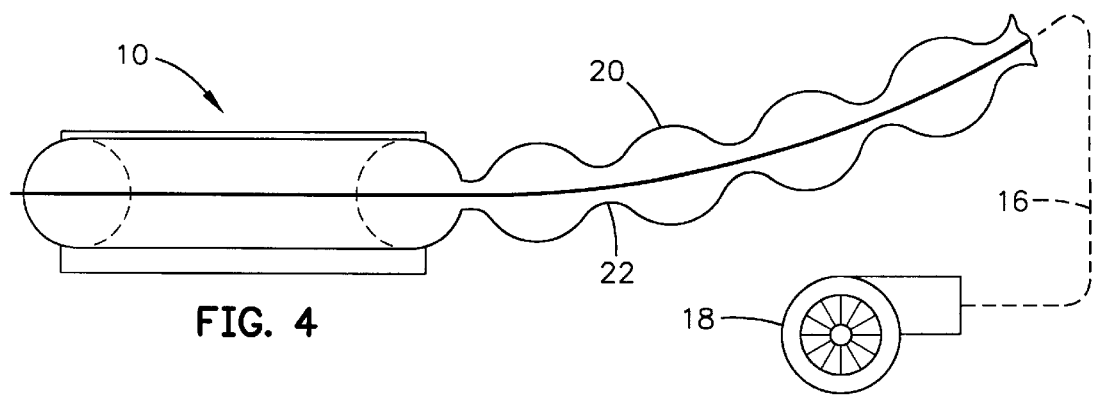
FIG. 4 is a side elevation view of a wound covering.

The apparatus, as illustrated in FIG. 4, is connected by suitable supply line or tube 16 to a source 18 of thermally controlled air which is schematically illustrated. The term air as used herein is intended to encompass mixtures of gases of controlled composition. The apparatus is constructed to apply a continuous stream of thermally controlled air to a wound treatment volume.

Figure 5:
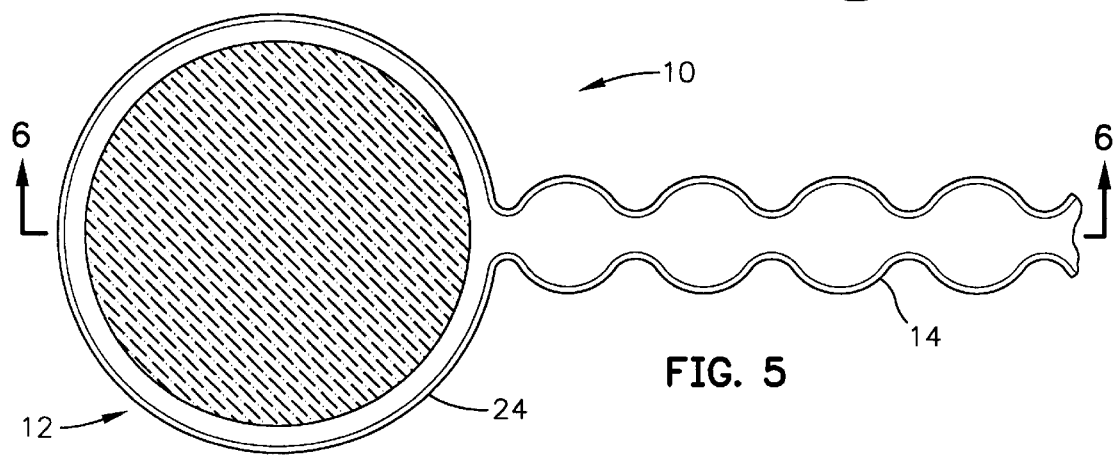
FIG. 5 is an enlarged top plan view of a wound covering.
Figure 6:
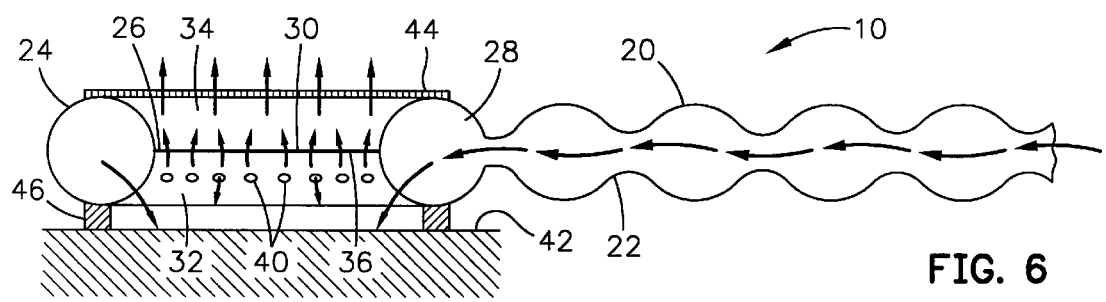
FIG. 6 is an enlarged sectional view taken along line 6—6 of FIG. 5.
Figure 7:
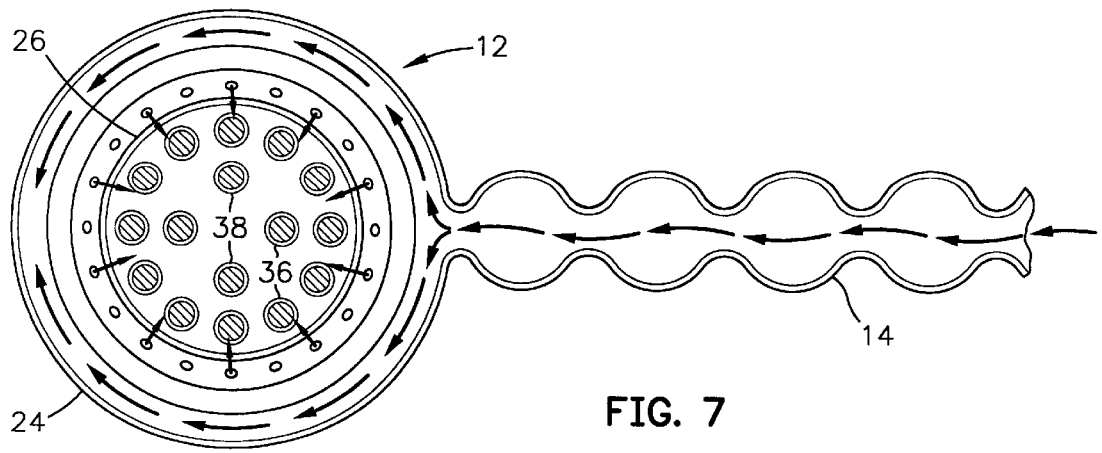
FIG. 7 is a bottom view of the wound covering of FIG. 4.

The specific form of the apparatus and details of construction can best be understood by reference to the various figures. The overall appearance of the wound covering is best seen in FIG. 4 and FIG. 5. It is preferred to construct the apparatus from top and bottom sheets of thin heat-sealable polymer film which overlay one another. A top sheet or membrane 20 overlies a bottom sheet or membrane 22 which are heat sealed together along a plurality of seal lines, including a continuous outer seam 24, which extends in a circle around head 12 and continues in a sinusoidal or convoluted fashion along and forming hose 14. An inner continuous circular seam 26 is provided as best seen in FIGS. 6 and 7. This inner seam 26 secures the sheets together along a continuous circle to form the inner wall of a torus defining a supply volume 28.

The inner circular portion of the two sheets 20, 22 lying in the plane within the center of the supply volume 28 forms a wall 30 separating a lower wound treatment volume 32 from an upper insulation chamber 34. Wall 30 includes a plurality of apertures 36 formed by making small circular seals 38 and cutting and removing circular portions within the circular seals 38. Thus, wall 30, with a plurality of apertures 36, is formed between the wound treatment volume 32 and insulation chamber 34. A plurality of apertures 40 are formed in the common circular wall surrounding treatment volume 32 for distributing and conveying heated air or gases from supply volume 28 into wound treatment volume 32.

The heated air flowing into treatment volume 32 bathes the wound surface of a patient's body 42. The air circulates throughout wound treatment volume 32, and then passes through apertures 36 into the upper or insulating chamber 34, where it then passes through a filter 44 forming an outer wall of insulation chamber 34. Filter 44 filters the air leaving wound treatment volume 32, trapping contaminants shed from the wound. Filter 44 may be constructed of a filter paper bonded along its periphery to the outer tangential walls of head 12 forming the torus. The filter paper also provides an insulating layer which suppresses loss of heat by radiation through upper wall 30.

The lower surface of the head 12 as shown in FIGS. 6 and 7 is provided with a peripheral sealing ring 46 made of an absorbent material such as foam and bonded by a suitable adhesive to the walls of head 12 and skin 42 of the patient around the wound. Preferably, foam or cotton peripheral sealing ring 46 is provided with a peel-off tape so that it adheres to the wall of the housing and on the other side to the slin of the patient. The adhesive or tape holds the apparatus in place and prevents airflow escape between the device and the skin of the patient. The absorbent material of the ring absorbs weeping blood and fluids and insulates the skin from direct conduction of heat from head 12.

Hose 14 is designed to be non-kinking by forming it of symmetrically convoluted flexible material. The hose and housing are integrally formed essentially of a unitary structure, such as a thin film membrane. Hose 14 is inflatable upon the application of heated air through supply line 16. The indentations in hose 14 permit it to bend without kinking and, thus, differentiate from a straight tubular hose which may kink when bent.

Since the thermal body treatment apparatus of the invention and the supply hose section are formed from two, thin, sealed-together membranes, the hose, and in fact the entire apparatus, is collapsible. This prevents the possibility of applying heat and pressure to the skin as might happen if a patient rolled over on the device. Instead, the weight of the patient's body collapses the device, obstructing the flow of air, and preventing the application of heat.

The film membrane may preferably be transparent to enable viewing the wound without removal. However for cosmetic reasons the layer may be opaque. Filter paper 44 is attached across the tangential surfaces of the toroidal housing, thus providing a large area of filter for the escaping air. Head 12 of the apparatus may be about one foot in diameter for most applications. However, it may be made smaller for certain other applications.

FIG. 8A illustrates an exploded view of an alternate embodiment of a non-contact wound covering 120 with climate control within a treatment volume 122 as shown in FIG. 8B. An inflatable structure 124 is preferably attached to a fluid inlet line 126 at a fluid inlet port 129 on the perimeter of inflatable structure 124. Inflatable structure 124 is preferably attached to an absorbent peripheral sealing ring 128, which is in turn attached to a wound area 54 by a suitable adhesive 56. Peripheral sealing ring 128 preferably has a sealed outer surface and a porous inner surface which performs the same function as peripheral sealing ring 52 discussed above. A barrier layer 130 having an exhaust filter 132 is attached to a top surface 134 on inflatable structure 124.

Turning now to the assembly illustrated in FIG. 8B, a gas, illustrated by direction arrows "A", is introduced into inflatable structure 124 from an external source (not shown) through inlet line 126. The gas pressurizes inflatable structure 124 in order to maintain barrier layer 130 and exhaust filter 132 in an elevated position relative to wound area 54. An inner surface 136 of inflatable structure 124 preferably has a plurality of apertures 138 through which the fluid is introduced into wound treatment volume 122. As pressure within the treatment chamber increases, excess pressure is relieved through exhaust filter 132. In this fashion, various fluids or gases can be introduced into wound treatment volume 122.

The use of the term "fluid" in the context of this application refers to both liquid and gaseous materials, and combinations thereof. In one embodiment, oxygen may be introduced into treatment volume 122 through apertures 138 of inflatable structure 124. The presence of oxygen within wound treatment volume 122 may increase the oxygen available to the superficial layer of growing cells in wound area 54. Nitric oxide alternatively may be infused into treatment volume 122. Nitric oxide (NO) is a potent vasodilator which in theory may be absorbed across the wound surface and increase localized blood flow. A very small concentration of NO (parts per million) may provide this effect. NO may also be pre-absorbed into absorbent peripheral sealing ring 128 and then allowed to passively diffuse into the volume once it is applied to the wound. Finally, gaseous or aerosolized medications or compounds may be introduced into the gas flow entering treatment volume 122.

FIGS. 9A and 9B illustrate an alternate embodiment of the climate control system discussed above wherein a fluid inlet line 140 may form part of a barrier layer 142. Barrier layer 142 is unitary with fluid inlet line 140 and is preferably attached to an exhaust filter media 144 to allow excess pressure to be released from a wound treatment volume 146. In this embodiment, filter media 144 forms part of barrier layer 142. The arrows "A" in FIG. 9B illustrate the movement of the fluid through fluid inlet line 140, treatment volume 146, and exhaust filter 144.

FIG. 10 illustrates an alternate embodiment wherein an exhaust filter 154 is retained in a recess 150 formed in one side of a peripheral sealing ring 152. This structure allows excess fluid to be exhausted through the side of peripheral sealing ring 152, rather than through the top, as illustrated in FIGS. 9A and 9B.

FIG. 11A is a perspective view of the embodiment illustrated in FIG. 9A, wherein a connector 160 on the end of a fluid supply line 162 engages with an opening 164 on fluid inlet line 140. FIG. 11B illustrates a side view of fluid supply line 162 as it engages with fluid inlet line 140. FIG. 11C illustrates the embodiment in FIGS. 11A and 11B where fluid inlet line 140 is folded over the top of peripheral sealing ring 152 to seal treatment volume 146 when supply line 162 is uncoupled.

Figure 12:
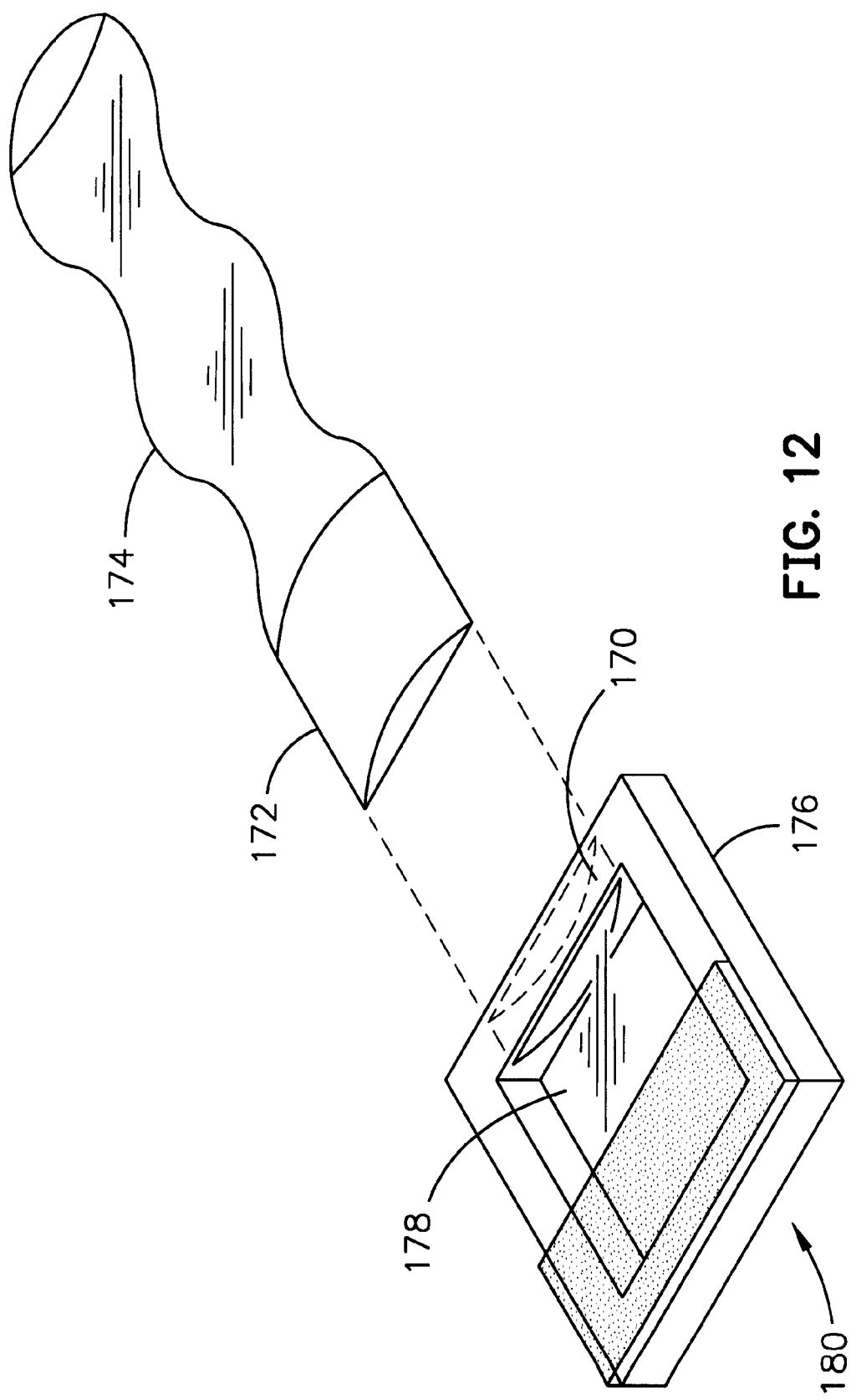
FIG. 12 is a perspective view of an alternate connector apparatus for the wound covering.

FIG. 12 illustrates an alternate embodiment in which a fluid inlet slot 170 engages with a rigid connector 172 on a fluid inlet line 174. Fluid inlet slot 170 forms an opening in one portion of a peripheral sealing ring 176. The opening is in fluid communication with a treatment volume 178. This configuration allows for quick disconnection of fluid inlet line 174 from wound covering 180 providing the patient with additional mobility.

Figure 14:
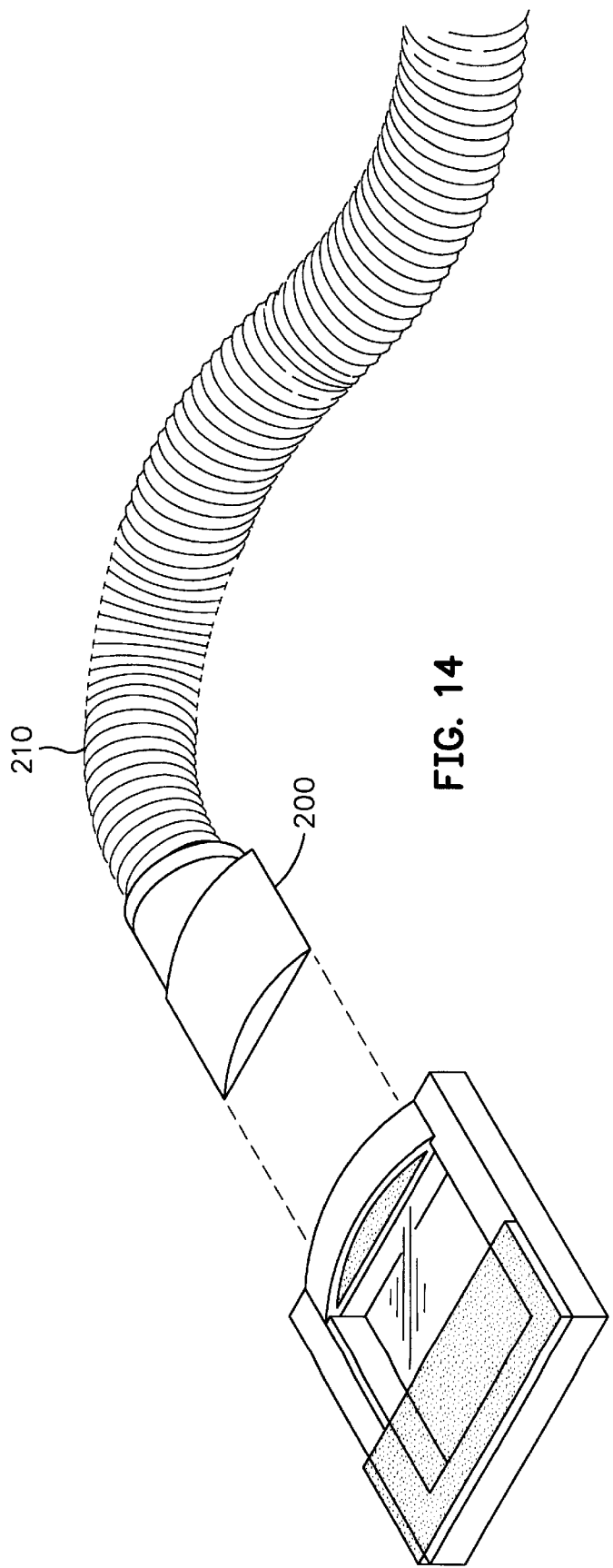
FIG. 14 is a view of a rigid connector for engagement with a wound covering.

FIG. 13A is a perspective view of an alternate non-contact wound covering 190 having a fluid inlet connector 192 attached to a top surface 194 of a peripheral sealing ring 196. Fluid inlet connector 192 preferably contains an inlet filter media 198. A rigid connector 200 on a fluid inlet line 202 mates with fluid inlet connector 192. As illustrated in FIG. 13B, a cover 204 extends from the top of fluid inlet connector 192 across the top of peripheral sealing ring 196 where it engages with an exhaust filter media 206. FIG. 14 illustrates the embodiment of FIGS. 13A and 13B utilizing a non-disposable fluid supply line 210.

Figure 15:
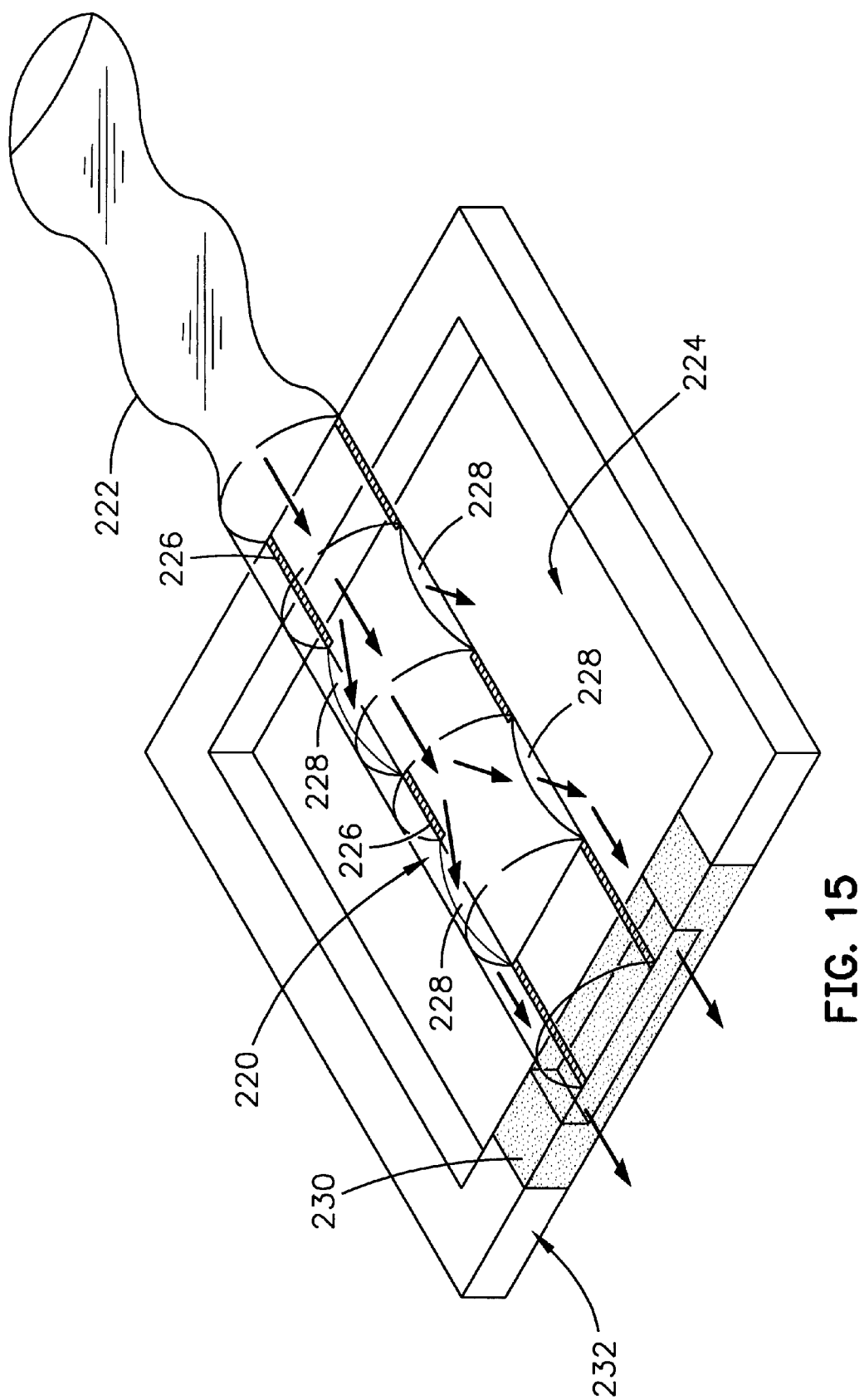
FIG. 15 is an alternate fluid inlet line for the wound covering.

FIG. 15 illustrates an alternate embodiment which utilizes a manifold structure 220 as part of a fluid inlet line 222 to provide even distribution of the fluid being introduced into a treatment volume 224. Fluid inlet line 222 preferably has a series of seals 226 along its edge which are interrupted by a plurality of side openings 228 from which the fluid can be transmitted into treatment volume 224. The embodiment disclosed in FIG. 15 illustrates an exhaust filter 230 recessed into the side of peripheral sealing ring 232. However, it will be understood that a variety of exhaust filter configurations are possible with the disclosed manifold structure 220.

FIGS. 16A and 16B illustrate an alternate wound covering 240 with a top barrier layer 242 and a lower layer 244 having a plurality of holes 246. As is illustrated in FIG. 16B, a top cover 243 forms the barrier layer 242 and it extends substantially across the area of the peripheral sealing ring 248. Lower layer 244 likewise extends across the peripheral sealing ring 248. Thus, an upper insulating layer 250 is formed between lower layer 244 and the top of barrier layer 242. Fluid in a fluid inlet line 252 is directed into upper insulating layer 250. The pressurized fluid in upper insulating layer 250 passes through holes 246 into a treatment volume 254. Holes 246 in lower layer 244 provide a generally even distribution of the fluid within wound treatment volume 254. An optional seal 258 may be formed in the center portion of barrier layer 242 and lower layer 244 to provide these layers with additional structural support. An exhaust filter medium 256 is provided in a recess along one side of peripheral sealing ring 248 to relieve pressure in treatment volume 254.

Figure 17:
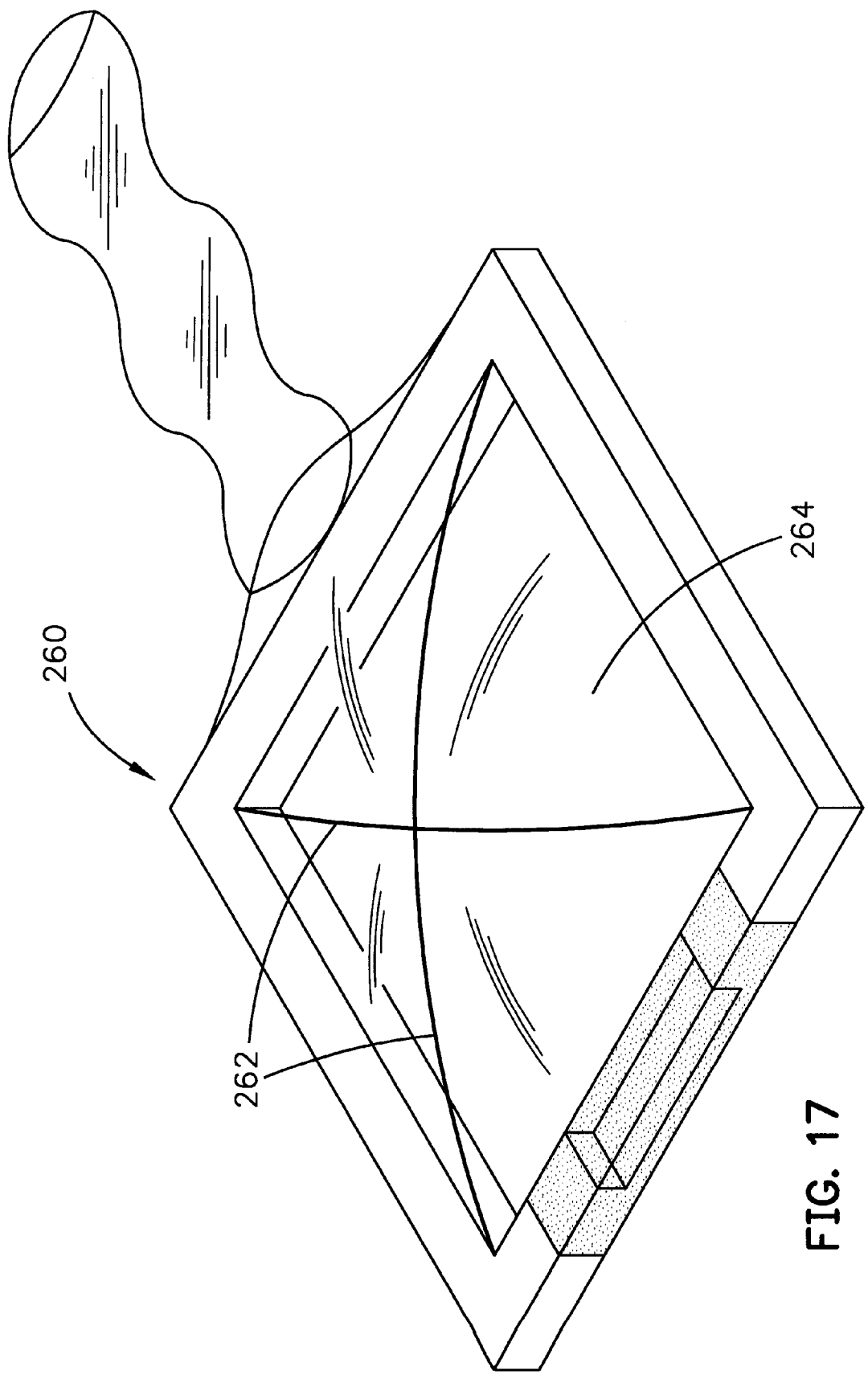
FIG. 17 is an alternate wound covering.

FIG. 17 illustrates an alternate embodiment of a non-contact wound covering 260 utilizing semi-rigid supports 262 to retain a barrier layer 264 above a wound area. It will be understood by those skilled in the art that a variety of semi-rigid supports 262 may be utilized for this application. For example, plastic or resilient rubber materials may provide sufficient support to barrier layer 264 with a minimum risk of injuring the patient.

FIGS. 18A and 18B illustrate an alternate exhaust filter medium 270 with an enlarged surface area to accommodate larger volumes of air flow through a non-contact wound covering 280. Exhaust filter 270 is incorporated into a fluid inlet line 272. Fluid inlet line 272 also forms a portion of a barrier layer 274, which is in turn attached to a peripheral sealing ring 276. As is best shown in FIG. 18B, fluid illustrated as the arrows "A" is introduced into a fluid inlet line 272, where it is directed into a wound treatment volume 278, past the wound area and out through exhaust filter medium 270.

Figure 19:
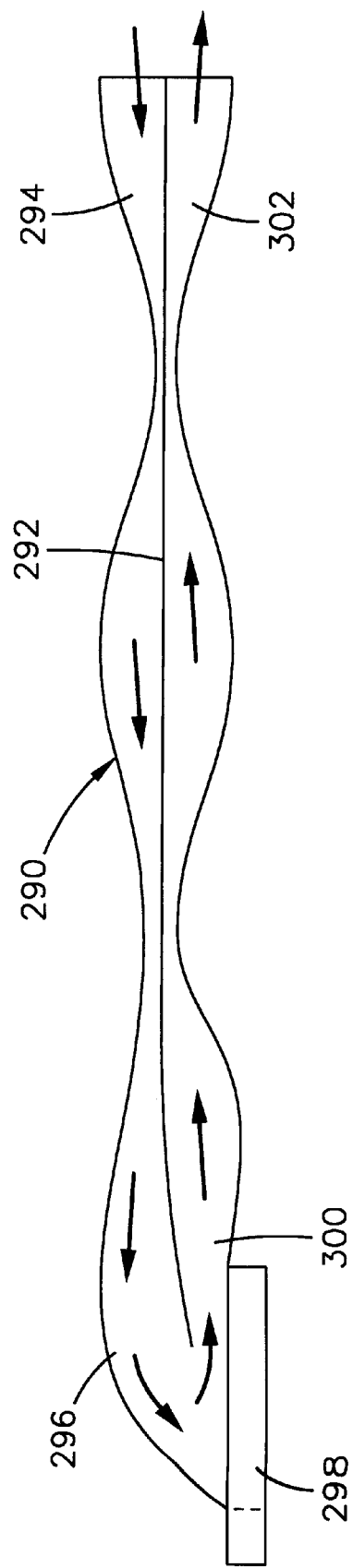
FIG. 19 is a side elevational view of an alternate wound covering

FIG. 19 illustrates a bidirectional line 290 with a center divider 292. Fluid is introduced into a fluid inlet line 294 where it proceeds through a fluid inlet port 296 into a treatment volume 298. The fluid then is forced through a fluid outlet port 300 where it is driven away from treatment volume 298 in a fluid outlet line 302. It will be understood by those skilled in the art that it would be possible to utilize separate fluid inlet and outlet lines to achieve the same result.

Figure 20:
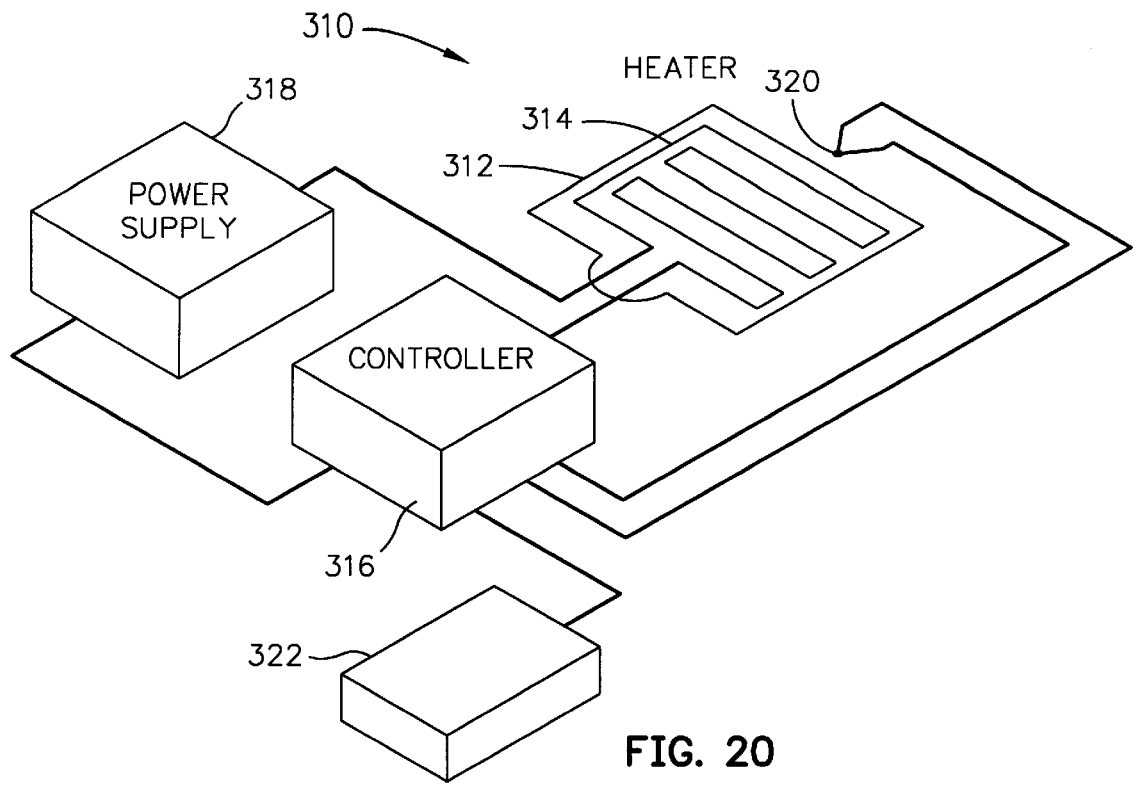
FIG. 20 is a schematic diagram of an embodiment of the present invention.

A schematic diagram of an embodiment of the present invention using active heating and control is depicted in FIG. 20 as an active heater assembly 310 including a heater 312, a heater filament 314 within heater 312, a controller 316, electrically coupled between heater filament 314 and a power source 318 by electrical connectors 315, and using a tissue temperature sensor 320, and an operator input interface 322 suitable for an operator to input programming parameters into controller 316. Heater assembly 310 is useful in several different configurations, for example, as providing a heater layer for use directly in a pocket such as that depicted by heater 100 inserted into pocket 114 shown in FIGS. 3A and 3B or as a heat source for warming air that is circulated over the wound as is depicted in the several embodiments of FIGS. 4 through 19.

Figure 21A:
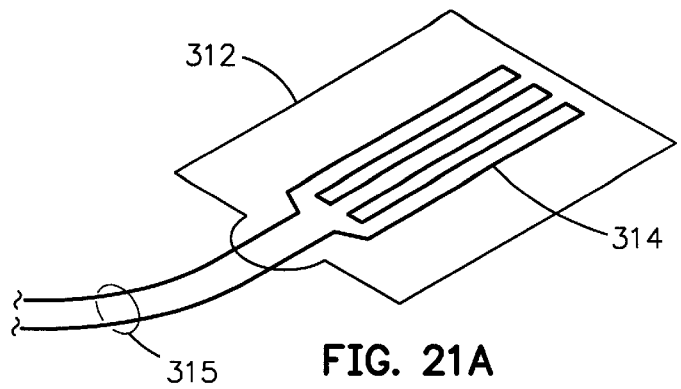
FIG. 21A is a schematic representation of an alternate embodiment of the heater array distribution shown in FIG. 20.
Figure 21B:
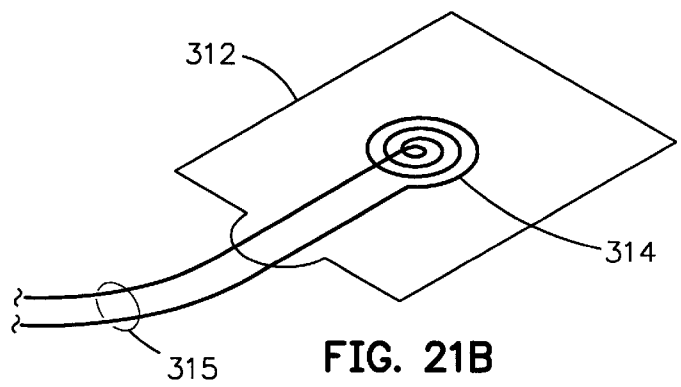
FIG. 21B is a schematic representation of an alternate embodiment of the heater array distribution shown in FIGS. 20 and 21A.
Figure 21C:
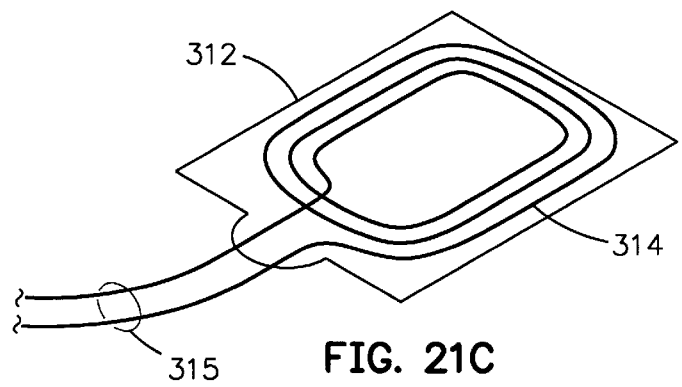
FIG. 21C is a schematic representation of an alternate embodiment of the heater array distribution shown in FIGS. 20, 21A, and 21B.
Figure 21D:
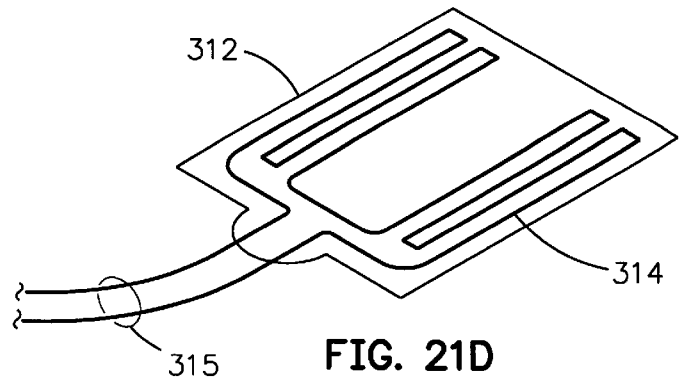
FIG. 21D is a schematic representation of an alternate embodiment of the heater array distribution shown in FIGS. 20, 21A, 21B, and 21C.

In addition to the various suggested fluid delivered heater "geometries" depicted in FIGS. 4–19, the present invention anticipates numerous possible heater electrical resistive filament 314 geometries. Examples of four such geometries are shown in FIGS. 21A, B, C, and D wherein there is depicted additional alternate heater array geometries for heating filament 314 within heater 312. In FIG. 21A, there is depicted a linear geometry for heater filament 314. This geometry is suitable for non-uniform heating where maximum heating is desired over a linear area, such as a linear surgical wound without direct heating over adjacent periwound areas. FIG. 21B depicts a geometry for heater filament 314 consistent more as a point source. FIG. 21C depicts an ovoid geometry for filament 314 suitable for non-uniform heating of selected periwound area. Alternatively, this non-uniform heating may be achievable with circular, square, rectangular, triangular or other such geometries depending on the type and shape of wound encountered.

In operation, heater assembly 310 is programmable, controlling one or more parameters, such as heater temperature, duty cycle, therapy cycle duration, number of duty cycles per therapy cycle, average heater temperature per duty cycle, and average heater temperature per therapy cycle. The programming may be preset at time of manufacture into controller 316 and provide a menu including treatment scenarios operator selectable at input interface 322. Additionally, the parameter programmability may be entirely under the control of an operator through input interface 322 and suitable for inputting any number of custom treatment regimens. For example, one regimen anticipates that an operator may input a desired tissue temperature and the target tissue is then monitored through tissue temperature sensor 320.

Alternatively, another regimen anticipates that an operator may input a treatment paradigm using parameters based on empirical modeling of tissue temperature responses for the various types of wounds, wound size, wound stage and wound location. Desired tissues targeted for monitoring may be the wound surface, the tissue below the wound surface, the periwound surface and tissue below the periwound surface. Empirical modeling may be based on parameters such as thermodynamic characteristics of tissue temperature conduction rates, surface area to be treated, tissue volume to be treated, wound type, wound location, wound staging, and heater geometries and heater outputs as a few of the paradigm values. Such programmable treatment paradigms are tissue temperature sensor independent and therefor tissue temperature sensor 320 is not needed in this mode.

Figure 22:
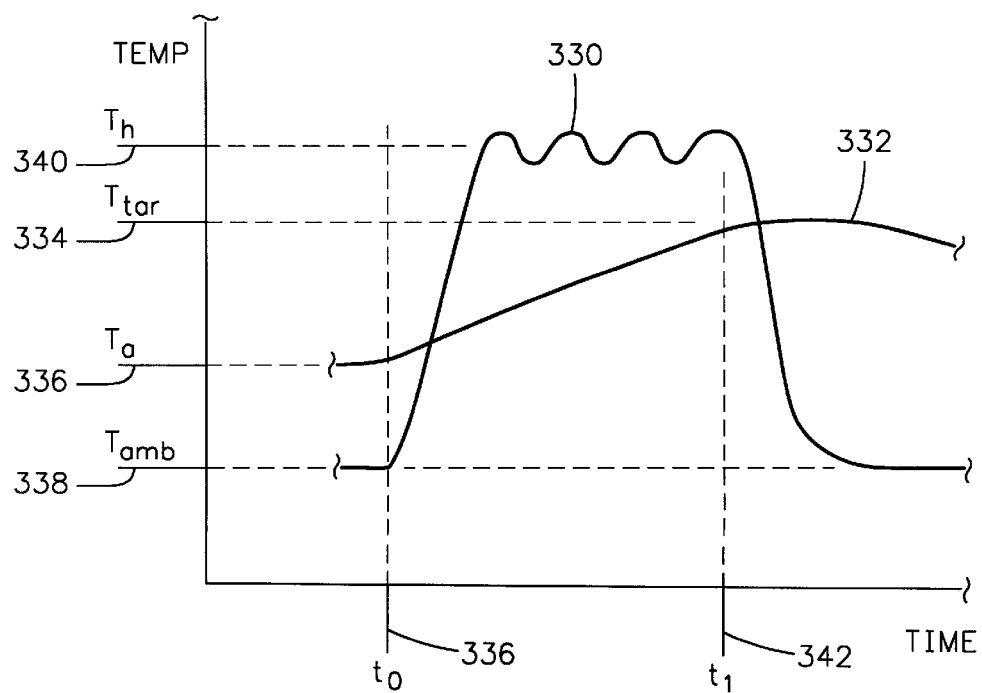
FIG. 22 is a graphical representative sample of an operational scheme for an embodiment of the present invention, such as the embodiment shown in FIG. 20.

By way of example, and not limiting in scope of treatment versatility, FIG. 22 is a graphic representation of one such treatment regimen. In FIG. 22, several heater duty cycles have been depicted as a curve 330 and the tissue temperature response as a curve 332. Time (t) is represented along the abscissa and temperature (T) along the ordinate. A tissue temperature target value $T_{tar}$ 334 has been entered either by program or direct input from the operator and the heater started at $t_0$ 334. The tissue start temperature is at a temperature $T_a$ 336 and the starting heater temperature is at ambient temperature $T_{amb}$ 338. By turning on the heater at $t_0$ 334, the first of several duty cycles for the heater begins in order to provide heat with which to raise the tissue temperature to $T_{tar}$ 334. A heater operating temperature $T_h$ 340 is chosen by the controller based on the value, either programmed or inputted, for $T_{tar}$ 334 and the heater controller provides the appropriate duty cycle ratio and heater cycle period so as to provide a safe and efficacious heating of at least a portion of the selected wound treatment area. The tissue target temperature $T_{tar}$ 334 value is reached at $t_1$ 342, at which time the heater is turned off. Alternatively, although not shown, upon reaching $T_{tar}$ 334, the controller could have changed $T_h$ 340 to a lower value and kept the heater active in order to maintain the tissue temperature at $T_{tar}$ 334.

Figure 23:
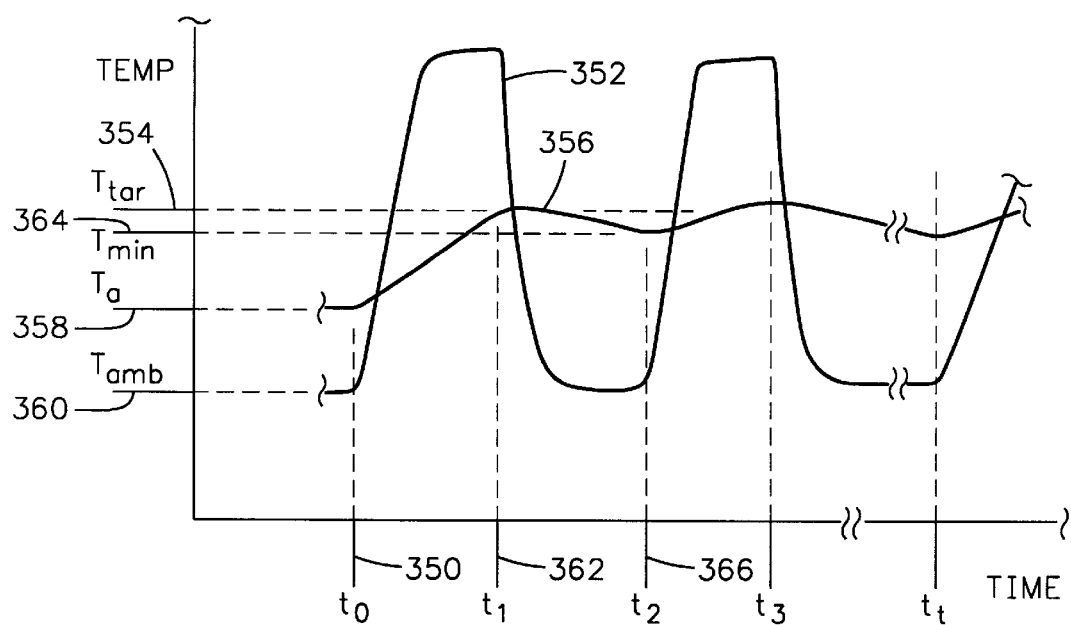
FIG. 23 is a graphical representative sample of an additional operational scheme for an embodiment of the present invention, such as the embodiment shown in FIG. 20 using the scheme depicted in FIG. 22.

By way of another example, and not limiting in scope of treatment versatility, a plurality of therapy cycles are depicted in FIG. 23, wherein individual heater cycles within each therapy cycle have been averaged out for purposes of clarification and for purposes herein are treated as the heater being "on". A first therapy cycle begins at $t_0$ 350 as depicted by the heater turning "on", i.e., a series of heater cycles is begun as shown by a heater temperature curve 352. A tissue temperature target value $T_{tar}$ 354 has been entered either by program or direct input from the operator and the tissue temperature response is shown in a curve 356. The tissue start temperature is at a temperature $T_a$ 358 and the starting heater temperature is at about ambient temperature $T_{amb}$ 360. The heater remains "on" until the tissue temperature has reached $T_{tar}$ 354 as monitored directly or as predicted by an appropriate heating paradigm. As shown $T_{tar}$ 354 is reached at $t_1$ 362 at which time the heater is turned "off". As in the previous example, an alternative is that the heater controller selects an alternate heating output, chosen to maintain the tissue temperature at about $T_{tar}$ 354. As depicted in FIG. 23, however, the tissue temperature is allowed to drift downwardly with the heater "off" until the tissue temperature reaches a temperature $T_{min}$ 364 that is either programmed or pre-selected as a value in the selected paradigm. Upon reaching $T_{min}$ 364, the heater is turned "on" again, as shown at $t_2$ 366, so as to provide heat to the selected treatment area to raise the tissue temperature to $T_{tar}$ 354. This first therapy cycle ends at $t_2$ 366 when a second therapy cycle begins by turning "on" the heater again. As in the first therapy cycle, this second therapy cycle provides heat to the tissue to reach the tissue target temperature, $T_{tar}$ 354. Alternatively this second therapy cycle may have a different $T_{tar}$ 354, or optionally may have a different cycle length calling for the controller to change the heater output. The present invention anticipates the use of any number of therapy cycles having any length or duration per cycle and different set temperatures, and a plurality of therapy cycles contributing to a therapeutic sequence.

Figure 24:
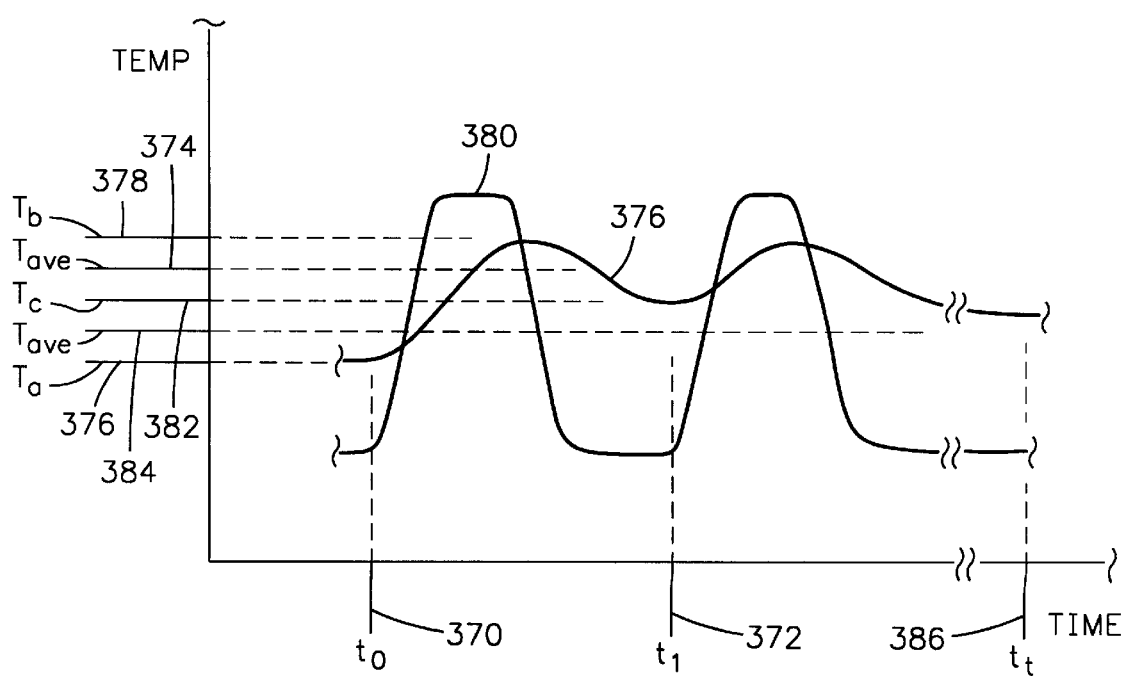
FIG. 24 is a graphical representative sample of another additional operational scheme for an embodiment of the present invention, such as the embodiment shown in FIG. 20 using the schemes depicted in FIGS. 22 and 23.

For the above examples, $T_{tar}$ 354 may be programmed as a paradigm or directly inputted into the controller. For the present invention, this tissue target temperature is in a range preferably from a pretreatment temperature to about 38° C. Another aspect of therapy control according to the present invention is the averaging of therapy cycle and therapeutic sequence tissue target temperatures, as depicted in FIG. 24. The example is not intended to be limiting in scope of treatment versatility.

In FIG. 24, a therapy cycle starts at $t_0$ 370 and ends at $t_1$ 372. The tissue target temperature average $T_{ave}$ 374 for this therapy cycle may be pre-selected or programmed. The tissue temperature change, as depicted by a temperature curve 376, begins at a temperature $T_a$ 376, rises as it is heated by the heater to $T_b$ 378 during the "on" phase of the heater, as depicted by a heater temperature curve 380, and then drifts downwardly to $T_c$ 382 over an additional period of time such that the total period of time is equivalent to the period $t_0$ 370 to $t_1$ 372. $T_{ave}$ 374 represents the average of the temperatures between $T_a$ 376 and $T_b$ 378, or in the alternative the average between $T_a$ 376 and $T_c$ 382 over the time period $t_0$ 370 to $t_1$ 372.

An alternative approach, also depicted in FIG. 24, anticipates the programming of a number of therapy cycles as elements of a therapeutic sequence, in this example there being two therapy cycles of varying times and tissue target temperatures. The present invention provides for the inputting of an average tissue target temperature $T_{ave}$ 384 for the therapeutic sequence, in this example, extending from $t_0$ 370 to $t_t$ 386. Each of these average temperatures, whether an average over a therapy cycle or over a therapeutic sequence, is intended to have the same temperature range from a pretreatment temperature to about 38° C. A secondary consequence of this controller regimen is that if average temperatures are used, either over the therapy cycle and/or therapeutic sequence, then the resultant peak tissue temperatures may be higher than this range. These peak temperatures are short lived by comparison and do not represent a safety concern.

The present invention is the development of a safe, efficacious non-contact heater wound covering providing heat to a patient's wound from the heater that warms a target tissue controlled to a temperature in a range from a pretreatment temperature to about 38° C., or controlled to an average temperature in a range from a pretreatment temperature to about 38° C. While the invention has been illustrated by means of specific embodiments and examples of use, it will be evident to those skilled in the art that many variations and modifications may be made therein without deviating from the scope and spirit of the invention. However, it is to be understood that the scope of the present invention is to be limited only by the appended claims.

TABLE 1

| Time (in minutes) | Subcutaneous Temperature (°C. mean ± S.D.) |
| --- | --- |
| −60 | 33.9 ± 1.1 |
| 0 | 34.7 ± 1.2 |
| 30 | 36.9 ± 0.6 |
| 60 | 37.1 ± 0.4 |
| 90 | 37.4 ± 0.5 |
| 120 | 37.6 ± 0.5 |
| 180 | 36.0 ± 0.4 |
| 240 | 36.1 ± 0.2 |
| 300 | 35.8 ± 0.6 |

TABLE 2

| Time (in minutes) | Skin Temperature Inside Covering (°C. mean ± S.D.) |
| --- | --- |
| −60 | 33.2 ± 1.1 |
| 0 | 33.9 ± 1.1 |
| 30 | 36.7 ± 0.5 |
| 60 | 37.0 ± 0.4 |
| 90 | 37.1 ± 0.4 |
| 120 | 37.2 ± 0.4 |
| 180 | 35.2 ± 0.5 |
| 240 | 35.2 ± 0.4 |
| 300 | 35.1 ± 0.5 |

TABLE 3

| Time (in minutes) | Laser Doppler Flow (ml/100g/min mean ± S.D.) |
| --- | --- |
| −60 | 64 ± 42 |
| 0 | 110 ± 100 |
| 30 | 199 ± 191 |
| 60 | 178 ± 131 |
| 90 | 222 ± 143 |
| 120 | 271 ± 235 |
| 180 | 158 ± 146 |
| 240 | 146 ± 125 |
| 300 | 173 ± 158 |

TABLE 4

| Time (in minutes) | Subcutaneous Oxygen Tension ($P_{sq}O_2$) (mm Hg mean ± S.D.) |
| --- | --- |
| −60 | 54 ± 10 |
| 0 | 110 ± 60 |
| 30 | 109 ± 58 |
| 60 | 122 ± 59 |
| 90 | 136 ± 57 |
| 120 | 159 ± 55 |
| 180 | 153 ± 60 |
| 240 | 156 ± 61 |
| 300 | 148 ± 52 |

TABLE 5

| Time (in minutes) | Subcutaneous Temperature (°C.) |
| --- | --- |
| −60 | 33.8 ± 1.5 |
| 0 | 35.2 ± 1.5 |
| 30 | 37.1 ± 1.1 |
| 60 | 37.3 ± 0.8 |
| 90 | 37.4 ± 0.7 |
| 120 | 37.3 ± 0.8 |
| 180 | 35.8 ± 1.2 |
| 240 | 35.8 ± 1.0 |
| 300 | 36.1 ± 0.9 |

TABLE 6

| Time (in minutes) | Skin Temperature Inside Covering (°C.) |
| --- | --- |
| −60 | 32.9 ± 1.5 |
| 0 | 34.5 ± 1.0 |
| 30 | 37.1 ± 0.6 |
| 60 | 37.5 ± 0.5 |
| 90 | 37.6 ± 0.5 |
| 120 | 37.6 ± 0.5 |
| 180 | 34.9 ± 0.8 |
| 240 | 35.0 ± 0.7 |
| 300 | 35.2 ± 0.6 |

TABLE 7

| Time (in minutes) | Laser Doppler Flow (ml/100g/min) |
| --- | --- |
| −60 | 44 ± 22 |
| 0 | 95 ± 132 |
| 30 | 142 ± 155 |
| 60 | 191 ± 150 |
| 90 | 207 ± 209 |
| 120 | 161 ± 91 |
| 180 | 73 ± 29 |

TABLE 7-continued

| Time (in minutes) | Laser Doppler Flow (ml/100g/min) |
|---|---|
| 240 | 70 ± 30 |
| 300 | 71.5 ± 25 |

TABLE 8

| Time (in minutes) | Subcutaneous Oxygen Tension ($P_{sq}O_2$) (mm Hg) |
|---|---|
| −60 | 58 ± 11 |
| 0 | 123 ± 73 |
| 30 | 128 ± 67 |
| 60 | 145 ± 69 |
| 90 | 157 ± 73 |
| 120 | 153 ± 55 |
| 180 | 148 ± 73 |
| 240 | 142 ± 73 |
| 300 | 143 ± 76 |

What is claimed:

1. A wound covering for application to a selected treatment area of a person's body, the selected treatment area including a wound area, said wound covering comprising:
    a heater for providing heat to at least a portion of the selected treatment area;
    a flexible attachment member for attaching the heater in a non-contact position proximate the selected treatnent area, said flexible attachment member including a peripheral sealing ring having an upper surface and a lower surface, said upper surface having a substantially continuous layer extending thereacross for support of the heater, said lower surface having an adhesive layer thereon for attaching the member around the selected treatment area, wherein neither the heater nor the member contacts the wound area; and
    a controller connected to the heater, for controlling the output of the heater to raise the temperature of the selected treatment area fom a pretreatment temperature to about 38° C.

2. The wound covering of claim 1 in which the heater includes an electrically resistive filament.

3. The wound covering of claim 1 in which the heater comprises a source of heat selected from the group consisting of: warm water pads, exothermic chemical heating pads, and phase-change salt pads.

4. The wound covering of claim 1 in which the heater is for uniformly heating the selected treatment area.

5. The would covering of claim 1 in which the heater is for non-uniform heating of the selected treatment area.

6. The wound covering of claim 1 in which the sealing ring defines an open cavity and seals around the selected treatment area.

7. The wound covering of claim 6 in which the sealing ring comprises a conformal polymeric ring.

8. The wound covering of claim 7 in which the conformal polymeric ring includes a polymeric foam.

9. The wound covering of claim 1, the layer maintaining a treatment volume proximate the selected wound area.

10. The wound covering of claim 9 in which the layer comprises a flexible sheet material.

11. The wound covering of claim 10 in which the flexible sheet material comprises a polymeric film.

12. The wound covering of claim 11 in which the polymeric film is selected from a group of polymers consisting of: cellulose, cellulose acetate, polyethylene, poly-vinylchloride, polyurethane, and polypropylene.

13. The wound covering of claim 9 in which the layer comprises a gas permeable material.

14. The wound covering of claim 9 in which the layer is sealed to the flexible attachment member as a barrier layer.

15. The wound covering of claim 1 in which the flexible attachment member includes a pocket on the layer suitable for releasable attachment of the heater.

16. The wound covering of claim 1 further comprising a pressure response switch to turn off the heater when pressure is applied to the wound covering.

17. The wound covering of claim 1 further including a tissue temperature sensor connected to the controller and input means for inputting at least one operator selectable target tissue temperature to the controller.

18. The wound covering of claim 17 in which the tissue temperature sensor senses the temperature of a tissue chosen from a group of tissue types consisting of: wound surface, wound tissue below the wound surface, periwound surface, and tissue below the periwound surface.

19. The wound covering of claim 1 in which the controller includes input means for providing at least one parameter in a programmable treatment paradigm.

20. The wound covering of claim 19 in which the at least one parameter is chosen from a group of parameters consisting of: thermodynamics characteristic of tissue, heat conduction rate of tissue types, wound location, wound type, wound stage, wound blood flow, tissue surface area involved in the selected treatment area, tissue volume involved in the selected treatment area, heater geometry, heater output, heater surface area, and ambient temperature.

21. A wound covering for application to a selected treatment area of a person's body, the selected treatment area including a wound area, said wound covering comprising:
    a heater layer for providing heat to at least a portion of the selected treatment area;
    one or more supports to support the heater layer in a non-contact position proximate the selected treatment area, said one or more supports including a peripheral sealing ring having an upper surface and a lower surface, said upper surface having a substantially continuous layer extending thereacross for support of the heater layer, said lower surface having an adhesive layer thereon for attaching the one or more supports around the selected treatment area, wherein neither the heater layer nor the one or more supports contacts the wound area;
    a controller operably connected to the heater layer, for controlling the temperature of the heater layer; and
    an input interface operably connected to the controller, for inputting to the controller a tissue treatment regimen for the portion of selected treatment area receiving heat so as to reach a target tissue temperature in a range from a pretreatment temperature to about 38° C.

22. The wound covering of claim 21 in which the heater layer is for uniformly heating the selected wound area.

23. The wound covering of claim 21 in which the heater layer is for non-uniform heating of the selected wound area.

24. The wound covering of claim 21 in which the sealing ring defines an open cavity and seals around the selected treatment area.

25. The wound covering of claim 24 in which the sealing ring comprises a conformal polymeric ring.

26. The wound covering of claim 25 in which the conformal polymeric ring includes a polymeric foam.

27. The wound covering of claim 21 in which the layer maintains a treatment volume over the selected wound area.

28. The wound covering of claim 27 in which the layer includes sealing to the one or more supports as a barrier.

29. The wound covering of claim 21 in which the layer comprises a flexible sheet material.

30. The wound covering of claim 29 in which the flexible sheet material comprises a polymeric film.

31. The wound covering of claim 30 in which the polymeric film is selected from a group of polymers consisting of: cellulose, cellulose acetate, polyethylene, poly-vinylchloride, polyurethane, and polypropylene.

32. The wound covering of claim 29 in which the layer includes a gas permeable material.

33. The wound covering of claim 21 in which the attachment means includes a pocket on the layer for releasable attachment of the heater layer.

34. The wound covering of claim 21 in which the controller includes a tissue temperature sensor and the input interface provides for inputting at least one operator selectable target tissue temperature.

35. The wound covering of claim 34 in which the tissue temperature sensor senses the temperature of a tissue chosen from a group of tissue types consisting of: wound surface, wound tissue below the wound surface, periwound surface, and tissue below the periwound surface.

36. The wound covering of claim 21 in which the input interface includes at least one parameter in a programmable treatment paradigm.

37. The wound covering of claim 36 in which the at least one parameter is chosen from a group of parameters consisting of: thermodynamics characteristic of tissue, heat conduction rate of tissue types, wound location, wound type, wound stage, wound blood flow, tissue surface area involved in the selected treatment area, tissue volume involved in the selected treatment area, heater geometry, heater output, heater surface area, and ambient temperature.

38. A wound covering for application to a selected treatment area of a person's body, the selected treatment area including a wound area, said wound covering comprising:
   a heater for providing heat to at least a portion of the selected treatment area;
   a support for attaching the heater in a non-contact position proximate the selected treatment area, said support including a peripheral sealing ring having an upper surface and a lower surface, said upper surface having a substantially continuous layer extending thereacross for support of the heater, said lower surface having an adhesive layer thereon for attaching the support around the selected treatment area, wherein neither the heater nor the support contacts the wound area;
   a controller, operably connected to the heater, for controlling the temperature of the heater; and
   an interface, operably connected to the controller, for inputting to the controller a tissue treatment regimen for the portion of selected treatment area receiving heat so as to reach an average target tissue temperature in a range from above a pretreatment temperature to about 38° C.

39. The wound covering of claim 38 in which the heater includes an electrically resistive filament.

40. The wound covering of claim 38 in which the heater comprises a source of heat selected from the group consisting of: warm water pads, exothermic chemical heating pads, and phase-change salt pads.

41. The wound covering of claim 38 in which the heater is for uniformly heating the selected treatment area.

42. The wound covering of claim 38 in which the heater is for non-uniform heating of the selected treatment area.

43. The wound covering of claim 38 in which the sealing ring defines an open cavity and seals around the selected treatment area.

44. The wound covering of claim 43 in which the sealing ring comprises a conformal polymeric ring.

45. The wound covering of claim 44 in which the conformal polymeric ring includes a polymeric foam.

46. The wound covering of claim 38 wherein the layer maintains a treatment volume proximate the selected wound area.

47. The wound covering of claim 46 in which the layer comprises a flexible sheet material.

48. The wound covering of claim 47 in which the flexible sheet material comprises a polymeric film.

49. The wound covering of claim 48 in which the polymeric film is selected from a group of polymers consisting of: cellulose, cellulose acetate, polyethylene, poly-vinylchloride, polyurethane, and polypropylene.

50. The wound covering of claim 46 in which the layer comprises a gas permeable material.

51. The wound covering of claim 46 in which the layer is sealed to the support as a barrier layer.

52. The wound covering of claim 38 in which the support includes a pocket on the layer suitable for releasable attachment of the heater.

53. The wound covering of claim 38 further comprising a pressure response switch to turn off the heater when pressure is applied to the wound covering.

54. The wound covering of claim 38 in which the controller includes a tissue temperature sensor and the interface provides for inputting at least one operator selectable target tissue temperature.

55. The wound covering of claim 54 in which the tissue temperature sensor senses the temperature of a tissue chosen from a group of tissue types consisting of: wound surface, wound tissue below the wound surface, periwound surface, and tissue below the periwound surface.

56. The wound covering of claim 38 in which the interface includes at least one parameter in a programmable treatment paradigm.

57. The wound covering of claim 56 in which the at least one parameter is chosen from a group of parameters consisting of: thermodynamics characteristic of tissue, heat conduction rate of tissue types, wound location, wound type, wound stage, wound blood flow, tissue surface area involved in the selected treatment area, tissue volume involved in the selected treatment area, heater geometry, heater output, heater surface area, and ambient temperature.

58. A wound covering for treating a selected treatment area of a person's body, said wound covering comprising:
   a heater;
   a support to hold the heater in a non-contact position proximate a wound in the selected treatment are, said support including a peripheral sealing ring having an upper surface and a lower surface, said upper surface having a substantially continuous layer extending thereacross for support of the heater, said lower surface having an adhesive layer thereon for attaching the support around the selected treatment area, wherein neither the heater nor the support contacts the wound area;
   a programmable temperature controller connected to the heater; and
   programming for causing the controller to operate the heater according to a tissue treatment regimen for raising the temperature of the tissue in a portion of the selected treatment area to an average target tissue temperature in a range from above a pretreatment temperature to about 38° C.

59. The wound covering of claim 58 in which the heater is for uniformly heating the selected treatment area.

60. The wound covering of claim 58 in which the heater is for non-uniform heating of the selected treatment area.

61. The wound covering of claim 58 in which the sealing ring defines an open cavity and seals around the selected treatment area.

62. The wound covering of claim 61 in which the sealing ring comprises a conformal polymeric ring.

63. The wound covering of claim 62 in which the conformal polymeric ring includes a polymeric foam.

64. The wound covering of claim 58 in which the heater includes spanning the support for maintaining a treatment volume proximate the selected treatment area.

65. The wound covering of claim 58 in which the heater comprises a flexible sheet material.

66. The wound covering of claim 65 in which the heater includes a gas permeable material.

67. The wound covering of claim 65 in which the flexible sheet material comprises a polymeric film.

68. The wound covering of claim 67 in which the polymeric film is selected from a group of polymers consisting of: cellulose, cellulose acetate, polyethylene, poly-vinyl-chloride, polyurethane, and polypropylene.

69. The wound covering of claim 58 in which the support includes a pocket suitable for releasable attachment of the heater layer.

70. The wound covering of claim 58 in which the controller includes a tissue temperature sensor and the programming provides for inputting at least one operator selectable target tissue temperature.

71. The wound covering of claim 70 in which the tissue temperature sensor senses the temperature of a tissue chosen from a group of tissue types consisting of: wound surface, wound tissue below the wound surface, periwound surface, and tissue below the periwound surface.

72. The wound covering of claim 58 in which the programing includes at least one parameter in a programmable treatment paradigm.

73. The wound covering of claim 72 in which the at least one parameter is chosen from a group of parameters consisting of: thermodynamics characteristic of tissue, heat conduction rate of tissue types, wound location, wound type, wound stage, wound blood flow, tissue surface area involved in the selected treatment area, tissue volume involved in the selected treatment area, heater geometry, heater output, heater surface area, and ambient temperature.

74. A method for treating a wound of a person, the method comprising the steps of:

selecting a wound treatment area of the person's skin including a target tissue near a wound;

providing a heater;

providing a controller operably connected to the heater;

forming a wound treatment volume over the wound by placing an enclosure over the wound treatment area, out of contact with the wound, said enclosure including a peripheral sealing ring having an upper surface and a lower surface, said upper surface having a substantially continuous layer extending thereacross for support of the heater, said lower surface having an adhesive layer thereon for attaching the enclosure around the selected treatment area;

attaching the heater to the enclosure, out of contact with the wound;

heating at least the target tissue; and causing the controller to operate the heater according to a tissue treatment regimen in which the target tissue receives heat;

the tissue treatment regime including operating the heater so as to heat at least the target tissue to a temperature in a range from a pretreatment temperature to about 38° C.

75. The method of claim 74 further comprising the step of programming the controller to operate the heater over a therapy cycle.

76. The method of claim 74 further comprising the step of programming the controller to operate the heater over a therapeutic sequence.

77. The method of claim 74 in which the tissue treatment regime includes controlling the temperature of at least the target tissue at an average temperature.

78. The method of claim 77 further comprising the step of programming the controller to operate the heater by maintaining an average temperature of the target tissue over a therapy cycle.

79. The method of claim 77 further comprising the step of programming the controller to operate the heater by maintaining an average temperature of the target tissue over a therapeutic sequence.

80. The method of claim 74 further comprising the step of inputting a target tissue temperature value to the controller in a temperature range a pretreatment temperature to about 38° C.

81. The method of claim 74 further comprising the step of inputting an average target tissue temperature value to the controller in an temperature range from a pretreatment temperature to about 38° C.

82. A wound covering, comprising:

a flexible sealing member defining a volume and including an upper surface and a lower surface;

a substantially continuous layer extending across the upper surface;

a heater supported against the upper surface by the layer;

an adhesive supported against the lower surface for attaching the flexible sealing member to a person in order to place the volume over a wound such that the member and the heater are out of contact with the wound; and a controller connected to the heater for causing the heater to raise a temperature of a selected temperature area including a wound from a pretreatment temperature to about 38° C.

83. The wound covering of claim 82, wherein the flexible sealing member includes a sealing ring.

84. The wound covering of claim 83, wherein the sealing ring is formed from polymeric foam.

85. The wound covering of claim 82, wherein the layer is a barrier layer.

86. The wound covering of claim 85, further including a pocket in the barrier layer in which the heater is received.

87. The wound covering of claim 82, the controller including programmable means for causing the heater to operate according to a therapy cycle in which the temperature of the selected treatment area is an average temperature.

* * * * *

UNITED STATES PATENT AND TRADEMARK OFFICE
CERTIFICATE OF CORRECTION

PATENT NO. : 5,964,723
DATED : October 12, 1999
INVENTOR(S) : Scott D. Augustine It is certified that error appears in the above-identified patent and that said Letters Patent is hereby corrected as shown below:

Title page,
Item [63], Related U.S. Application Data, after "08/356,325, filed" please delete "as application" and insert the following:
-- February 21, 1995, now abandoned, which is a 35 U.S.C. § 371 application of PCT international application Serial --; after "PCT/US93/05876" please delete "abandoned,"

Signed and Sealed this

First Day of June, 2004

JON W. DUDAS
*Acting Director of the United States Patent and Trademark Office*